United States Patent
Haick et al.

(10) Patent No.: US 9,359,197 B2
(45) Date of Patent: Jun. 7, 2016

(54) METHOD OF DIAGNOSING, PROGNOSING AND MONITORING PARKINSON'S DISEASE

(75) Inventors: Hossam Haick, Haifa (IL); Abraham Marmur, Haifa (IL); Urike Tisch, Haifa (IL)

(73) Assignee: TECHNION RESEARCH & DEVELOPMENT FOUNDATION LTD., Haifa (IL)

( * ) Notice: Subject to any disclaimer, the term of this patent is extended or adjusted under 35 U.S.C. 154(b) by 895 days.

(21) Appl. No.: 13/424,685

(22) Filed: Mar. 20, 2012

(65) Prior Publication Data
US 2012/0245434 A1  Sep. 27, 2012

Related U.S. Application Data

(60) Provisional application No. 61/466,962, filed on Mar. 24, 2011, provisional application No. 61/471,217, filed on Apr. 4, 2011.

(51) Int. Cl.
| | |
|---|---|
| *A61B 5/08* | (2006.01) |
| *B82Y 5/00* | (2011.01) |
| *B82Y 15/00* | (2011.01) |
| *A61B 5/00* | (2006.01) |
| *G06F 19/00* | (2011.01) |

(52) U.S. Cl.
CPC . *B82Y 5/00* (2013.01); *A61B 5/082* (2013.01); *A61B 5/4082* (2013.01); *A61B 5/4842* (2013.01); *B82Y 15/00* (2013.01); *G06F 19/707* (2013.01)

(58) Field of Classification Search
USPC .......................................... 600/300; 977/773
See application file for complete search history.

(56) References Cited

U.S. PATENT DOCUMENTS

| | | | |
|---|---|---|---|
| 6,610,270 B1 | 8/2003 | Ajami | |
| 2002/0081745 A1* | 6/2002 | Ross et al. | 436/141 |
| 2010/0273665 A1* | 10/2010 | Haick et al. | 506/8 |
| 2011/0244584 A1* | 10/2011 | Haick et al. | 436/71 |
| 2011/0269632 A1* | 11/2011 | Haick et al. | 506/7 |

FOREIGN PATENT DOCUMENTS

| | | |
|---|---|---|
| WO | 00/00636 A1 | 1/2000 |
| WO | 00/61002 A1 | 10/2000 |
| WO | 03/094932 A1 | 11/2003 |
| WO | 2005/079669 | 9/2005 |
| WO | 2007/045865 | 4/2007 |

(Continued)

OTHER PUBLICATIONS

Barba et al., (2008) Alzheimer's disease beyond the genomic era: nuclear magnetic resonance (NMR) spectroscopy-based metabolomics. J Cell Mol Med 12(5A):1477-1485.

(Continued)

*Primary Examiner* — Michael Kahelin
*Assistant Examiner* — Mitchell E Alter
(74) *Attorney, Agent, or Firm* — Knobbe, Martens, Olson & Bear, LLP

(57) ABSTRACT

The present invention provides a system and method for diagnosing, monitoring, prognosing or staging Parkinson's disease using at least one sensor comprising carbon nanotubes coated with cyclodextrin or derivatives thereof or metal nanoparticles coated with various organic coatings in conjunction with a learning and pattern recognition algorithm.

25 Claims, 6 Drawing Sheets

(56) References Cited

FOREIGN PATENT DOCUMENTS

| WO | 2007/086986 | | 8/2007 |
|---|---|---|---|
| WO | 2008/124187 | A1 | 10/2008 |
| WO | 2009/066293 | A1 | 5/2009 |
| WO | 2009/144725 | A1 | 12/2009 |
| WO | 2010/040097 | | 4/2010 |
| WO | 2010/064239 | A1 | 6/2010 |
| WO | 2010/066000 | A1 | 6/2010 |
| WO | 2010/079490 | A1 | 7/2010 |
| WO | 2011/010103 | | 1/2011 |

OTHER PUBLICATIONS

Ewers et al., (2010) Blood-based biomarkers of microvascular pathology in Alzheimer's disease. Exp Gerontol 45(1):75-79.
Hu et al., (2010) Biomarker discovery for Alzheimer's disease, frontotemporal lobar degeneration, and Parkinson's disease. Acta Neuropathol 120(3):385-399.
Ahmed, Sheik SSJ et al., (2009) Metabolic profiling of Parkinson's disease: evidence of biomarker from gene expression analysis and rapid neural network detection. J Biomed Sci 16(1):63.
Amann, A. et al., (2010) Chapter 7: Methodological issues of sample collection and analysis of exhaled breath. European Respiratory Society Monograph 49:96-114.
Baykal, Ahmet T. et al., (2008) Aberrant regulation of choline metabolism by mitochondrial electron transport system inhibition in neuroblastoma cells. Metabolomics 4(4):347-356.
Bogdanov, Mikhail et al., (2008) Metabolomic profiling to develop blood biomarkers for Parkinson's disease. Brain 131(pt 2):389-96.
Brust, Mathias et al., (1994) Synthesis of thiol-derivatised gold nanoparticles in a two-phase Liquid-Liquid system . J Chem Soc Chem Commun 1994(7):801-802.
Coelho, Leiliane et al., (2007) Breath air analysis and its use as a biomarker in biological monitoring of occupational and environmental exposure to chemical agents. J Chromatography B 853(1-2):1-9.
Dovgolevsky, Ekaterina and Haick, Hossam (2008) Direct observation of the transition point between quasi-spherical and cubic nanoparticles in a two-step seed-mediated growth method. Small 4(11):2059-2066 Epub Oct. 17, 2008.
Dovgolevsky, Ekaterina et al., (2009) Chemically sensitive resistors based on monolayer-capped cubic nanoparticles: towards configurable nanoporous sensors. Small 5(10):1158-1161 Epub Mar 9, 2009.
Goetz, Christopher G. et al., (2004) Movement Disorder Society Task Force report on the Hoehn and Yahr staging scale: status and recommendations. Mov Disord 19(9):1020-1028.
Greenberg, Nicola et al., (2009) A proposed metabolic strategy for monitoring disease progression in Alzheimer's disease. Electrophoresis 30(7):1235-1239 Epub Mar. 16, 2009.
Haick, Hossam et al., (2009) Sniffing chronic renal failure in rat model by an array of random networks of single-walled carbon nanotubes. ACS Nano 3(5):1258-1266.
Hoehn, Margaret M. and Yahr, Melvin D. (1967) Parkinsonism: onset, progression and mortality. Neurology 17 (5):427-442.
Hostetler, Michael J. et al., (1998) Alkanethiolate Gold Cluster Molecules with Core Diameters from 1.5 to 5.2 nm: Core and Monolayer Properties as a Function of Core Size. Langmuir 14(1):17-30.
Hughes, Andrew J. et al., (2002) The accuracy of diagnosis of parkinsonian syndromes in a specialist movement disorder service. Brain 125(pt 4):861-870.
Ionescu, R. et al., (2002) Quantitative analysis of $NO_2$ in the presence of CO using a single tungsten oxide semiconductor sensor and dynamic signal processing. Analyst 127(9):1237-1246.
Michell, Andrew W. et al., (2008) Metabolomic analysis of urine and serum in Parkinson's disease. Metabolomics 4(3):191-201.
Ouyang, Gangfeng and Pawliszyn, Janusz (2006) SPME in environmental analysis. Anal Bioanal Chem 386(4):1059-1073 Epub May 4, 2006.
Peng, Gang at al., (2008) Detecting simulated patterns of lung cancer biomarkers by random network of single-walled carbon nanotubes coated with nonpolymeric organic materials. Nano Lett 8(11):3631-3635 Epub Oct. 8, 2008.
Peng, Gang et al., (2009) Diagnosing lung cancer in exhaled breath using gold nanoparticles. Nat Nanotech 4(11):669-673.
Peng, G. et al., (2010) Detection of lung, breast, colorectal, and prostate cancers from exhaled breath using a single array of nanosensors. Br J Cancer 103(4):542-551 Epub Jul. 20, 2010.
Quinones, Marlon P. and Kaddurah-Daouk, Rima (2009) Metabolomics tools for identifying biomarkers for neuropsychiatric diseases. Neurobiol Dis 35(2)165-176 Epu Mar. 19, 2009.
Zhao, Xiao-Mei et al., (1997) Soft lithographic methods for nanofabrication. J Mater Chem 7(7):1069-1973.
Tisch et al., (2012) Detection of Asymptomatic Nigrostriatal Dopaminergic Lesion in Rats by Exhaled Air Analysis Using Carbon Nanotube Sensors. ACS Chem Neurosci 3(3): 161-166.

* cited by examiner

METHOD OF DIAGNOSING, PROGNOSING AND MONITORING PARKINSON'S DISEASE

FIELD OF THE INVENTION

The present invention relates to a system and methods for diagnosis, prognosis and monitoring of Parkinson's disease through breath analysis.

BACKGROUND OF THE INVENTION

Parkinson's disease (PD) is a progressive neurodegenerative disease whose primary clinical manifestation includes motor disorders such as dyskinesia, resting tremor, rigidity, and gait disturbance. PD is characterized by the loss of dopamine neurons in the substantia nigra pars compacta and the presence of inclusion bodies in the surviving neurons of the same region. Progression of these inclusion bodies to the various regions outside the midbrain may account for the abundance of the secondary symptoms commonly observed in PD patients, such as depression, dementia, and various autonomic and sensory dysfunctions.

PD affects more than 4 million people worldwide and is becoming more and more prevalent as the population ages. The diagnosis of PD mostly relies on clinical symptoms. Since the disease is characterized by a long pre-clinical phase, it is often diagnosed only after irreversible damage has already occurred. In specialist clinics, the positive predictive value of the clinical diagnosis of idiopathic PD can reach 99% with 91% sensitivity. However, outside the specialist setting, the predictive value is considerably lower (Hughes et al., Brain, 2002, 125, 861). PD progression is monitored using the Hoehn and Yahr (HY) scale (Hoehn et al., Neurology, 1967, 17, 427). Progressively higher stages correlate with neuroimaging studies of dopaminergic loss, and high correlations exist between the HY scale and some standardized scales of motor impairment, disability, and other parameters which impair the quality of life (Goetz et al., Mov. Disord., 2004, 19, 1020).

Correct and early diagnosis currently depends on the expertise of the treating physician. Although important progress has been made in biomarker research for PD, no validated biomarker is available to date (Michell et al., Metabolomics, 2008, 4, 191; Ahmed et al., J. Biomed. Sci., 2009, 16, 63; Bogdanov et al., Brain, 2008, 131, 389; Quinones et al., Neurobiol. Dis., 2009, 35, 165; Greenberg et al., Electrophoresis, 2009, 30, 1235).

Recent studies indicate that the metabolic changes which are associated with PD may be traced by metabolomic profiling (i.e. the identification of patterns of metabolomic biomarkers that together provide a characteristic fingerprint) in blood or urine samples. PD signatures and sets of relevant biomarkers (mostly derivatives of alkylamines, organic acids, and sugar alcohols) were derived through pattern recognition analysis (Michell et al., Metabolomics, 2008, 4, 191; Ahmed et al., J. Biomed. Sci., 2009, 16, 63; Bogdanov et al., Brain, 2008, 131, 389; Quinones et al., Neurobiol. Dis., 2009, 35, 165; Baykal et al., Metabolomics, 2008, 4, 347). The results of the plasma analysis show promising results for the development of early-stage diagnostics, and indicate that there might be a connection between disease progression and metabolite variation. However, blood sampling is invasive and requires time consuming laboratory procedures prior to analysis (e.g. agitation, incubation etc.).

WO 2010/066000 discloses a method for predicting the susceptibility of a subject to a mental or neurodegenerative disorder, including PD, the method comprising: (a) obtaining one or more biological samples from the subject; (b) determining the levels of one or more biomarkers in the sample, wherein the biomarkers are selected from pyrroles, histamine, methionine adenosyltransferase (MAT) activity, homocysteine, copper and zinc; and (c) comparing the level(s) of the biomarker(s) determined in (b) with the level(s) of said biomarker(s) from one or more control samples, wherein abnormal levels of the one or more biomarkers in the sample(s) from the subject compared to the one or more control samples is predictive of susceptibility of the subject to a mental or neurodegenerative disorder.

WO 2000/000636 discloses a method of determining the in vivo conversion activity of a Class I, II or III gateway enzyme, said method comprising the steps of: identifying a Class I, II or III gateway enzyme to be assayed; selecting a labelled metaprobe for said enzyme, said metaprobe being selected so that when acted upon by said enzyme, at least one labelled end product that is directly detectable is produced; administering to a patient a defined amount of said labelled metaprobe; and determining the extent of conversion of said metaprobe to said labelled end product by said enzyme.

WO 2008/124187 discloses a method for diagnosis or monitoring a disease or condition in an individual comprising: (a) collecting one or more biological sample from said individual, wherein the biological sample(s) contain proteins, lipids and nucleic acids of the individual; (b) analyzing the proteins and/or lipids from a biological sample to determine selective metabolites and oxidation products of arachidonic acid (AHA), docosahexanoic acid (DHA) and eicosapentaenoic acid (EPA); wherein said analyzing results in a metabolic determination of oxidative stress and lipids; and (c) analyzing the nucleic acids from a biological sample to determine the genotype and/or expression of genes involved in oxidative stress and/or lipid metabolism; wherein the existence or severity of a disease or condition is determined.

WO 2009/144725 to one of the inventors of the present application discloses a system for detecting volatile organic compounds derived from a breath sample, the system comprising: (a) an apparatus comprising an array of chemically sensitive sensors of single walled carbon nanotubes coated with non-polar small organic molecules, and (b) a processing unit comprising a learning and pattern recognition analyzer wherein the learning and pattern recognition analyzer receives sensor output signals and compares them to stored data.

WO 2010/064239 to one of the inventors of the present application discloses a system comprising an array of sensors for measuring volatile organic compounds as biomarkers for diagnosis, prognosis and monitoring of renal insufficiencies, the system comprises an array of sensors comprising a (semi-) conductive random network of single-walled carbon nanotubes (SWCNTs) coated with an organic coating which comprises oligomers or polymers modified with at least one polar functional group, in conjunction with learning and pattern recognition algorithms.

WO 2009/066293 to one of the inventors of the present application discloses an apparatus comprising at least one chemically sensitive sensor for detecting volatile and non-volatile compounds, wherein the chemically sensitive sensor comprises cubic nanoparticle conductive cores capped with an organic coating. Methods of use thereof in identifying various disease biomarkers, and in food quality and environmental control are disclosed.

WO 2010/079490 to one of the inventors of the present application discloses a sensor array for detecting biomarkers for cancer in breath samples. The sensor array is based on 2D films or 3D assemblies of conductive nanoparticles capped with an organic coating wherein the nanoparticles are characterized by a narrow size distribution.

WO 2003/094932 discloses the use of carbon monoxide (CO) as a biomarker and therapeutic agent of conditions and disease states including, inter alia, Parkinson's disease.

WO 2000/061002 discloses a method for the assessment of psychiatric or neurological conditions, including PD, the method comprising determining the presence and/or amount of ethane or butane in the expired breath of the patient.

At present, no simple and reliable technique is available for the early diagnosis of PD. Additionally, there remains an unmet need for monitoring Parkinson's disease progression using breath biomarkers thus affording adequate PD management.

SUMMARY OF THE INVENTION

The present invention provides a system and methods for diagnosing, monitoring, prognosing or staging Parkinson's disease in a subject.

The system and method of the present invention provide improved sensitivity and selectivity for diagnosis, prognosis and monitoring various stages of Parkinson's disease, and thus offer significant advantages over the prior art. The present invention is based in part on the unexpected finding that a sensor array comprising at least one sensor comprising a random network of carbon nanotubes coated with cyclodextrin or cyclodextrin derivatives and/or at least one sensor comprising metal nanoparticles capped with various organic coatings provide enhanced sensitivity and selectivity for volatile biomarkers in breath samples which are indicative of Parkinson's disease. The use of the sensor array in conjunction with a learning and pattern recognition algorithm provides information regarding the different stages of the disease. Thus, the present invention provides a fast and reliable differential diagnosis of PD allowing a comprehensive PD management, including monitoring of disease progression.

According to one aspect, the present invention provides a system for diagnosing, monitoring, prognosing or staging PD, the system comprising: (a) an apparatus comprising at least one sensor comprising nanomaterials selected from single walled carbon nanotubes coated with cyclodextrin or a derivative thereof and metal nanoparticles capped with an organic coating; (b) a detection means; and (c) a processing unit comprising a learning and pattern recognition analyzer wherein the learning and pattern recognition analyzer receives sensor output signals and compares them to stored data.

In one embodiment, the cyclodextrin or cyclodextrin derivative is selected from the group consisting of α-cyclodextrin, β-cyclodextrin, γ-cyclodextrin, methyl-β-cyclodextrin, 2,6-dibutyl-β-cyclodextrin, hydroxypropyl-β-cyclodextrin, 2,6-di-O-methyl-β-cyclodextrin, permethylated α-cyclodextrin-6$^A$-monoalcohol nitrate, dinitrophenyl substituted β-cyclodextrin-based chiral stationary phases, β- and γ-cyclodextrins bearing 4-amino-7-nitrobenz-2-oxa-1,3-diazole functional groups, sulfated and carboxy-methylated β-cyclodextrins, mono(6-cyclohexylamino-6-deoxy)-β-cyclodextrin, mono-(6-benzyl-imino-6-deoxy)-β-cyclodextrin, mono[6-(o-amino-phenyl)imino-6-deoxy]-β-cyclodextrin, mono[6-(p-aminophenyl)imino-6-deoxy]-β-cyclodextrin, mono[6-(α-naphthyl)imino-6-deoxy]-β-cyclodextrin, hexakis(6-O-benzoyl)-α-cyclodextrin, heptakis(2,3,6-tri-O-benzoyl)-β-cyclodextrin, heptakis(2,3,6-tri-O-methyl)-β-cyclodextrin, hexakis(6-O-benzoyl-2,3-di-O-benzyl)-α-cyclodextrin, hexakis(2,3-di-O-benzyl)-α-cyclodextrin, 2-6-amino-β-cyclodextrin, permethylated-β-cyclodextrin, 2A,3A-Alloepithio-2A,3A-dideoxy-β-cyclodextrin, and combinations thereof. Each possibility represents a separate embodiment of the present invention.

In another embodiment, the cyclodextrin or cyclodextrin derivative is selected from the group consisting of α-cyclodextrin, carboxy-methylated β-cyclodextrin, heptakis(2,3,6-tri-O-methyl)-β-cyclodextrin and combinations thereof. Each possibility represents a separate embodiment of the present invention.

In yet another embodiment, the single walled carbon nanotubes are organized in a random network configuration.

In other embodiments, the single walled carbon nanotubes have diameters ranging from about 0.9 nanometer to about 5 nanometers, and lengths ranging from about 1 micrometer to about 50 micrometers.

In further embodiments, the metal nanoparticles are selected from the group consisting of Au, Ag, Ni, Co, Pt, Pd, Cu, and Al nanoparticles. Each possibility represents a separate embodiment of the present invention.

In some embodiments, the organic coating of the metal nanoparticles comprises compounds selected from the group consisting of alkylthiols, arylthiols, alkylarylthiols, alkylthiolates, ω-functionalized alkanethiolates, arenethiolates, (γ-mercaptopropyl)tri-methyloxysilane, dialkyl disulfides and combinations and derivatives thereof. Each possibility represents a separate embodiment of the present invention.

In particular embodiments, the organic coating of the metal nanoparticles is selected from the group consisting of 3-mercapto-propionate, 2-mercapto-benzoazole, 11-mercapto-1-undecanol and combinations thereof. Each possibility represents a separate embodiment of the present invention.

In other embodiments, the metal nanoparticles have a morphology selected from a cubic, a spherical, and a spheroidal morphology. Each possibility represents a separate embodiment of the invention.

In certain embodiments, the at least one sensor is configured in a form selected from the group consisting of a capacitive sensor, a resistive sensor, an impedance sensor, and a field effect transistor sensor. Each possibility represents a separate embodiment of the present invention.

In some embodiments, the system comprises a single sensor.

In other embodiments, the system comprises a plurality of sensors, for example between 2 and 6 sensors. In additional embodiments, the plurality of sensors comprises at least one sensor comprising single walled carbon nanotubes coated with cyclodextrin or a derivative thereof and at least one sensor comprising metal nanoparticles capped with an organic coating.

In other embodiments, the detection means comprises a device for measuring changes in resistance, conductance, alternating current (AC), frequency, capacitance, impedance, inductance, mobility, electrical potential, optical property or voltage threshold. Each possibility represents a separate embodiment of the present invention.

In further embodiments, the learning and pattern recognition analyzer comprises at least one algorithm selected from the group consisting of artificial neural network algorithms, principal component analysis (PCA), multi-layer perception (MLP), generalized regression neural network (GRNN), fuzzy inference systems (FIS), self-organizing map (SOM), radial bias function (RBF), genetic algorithms (GAS), neuro-fuzzy systems (NFS), adaptive resonance theory (ART), partial least squares (PLS), multiple linear regression (MLR), principal component regression (PCR), discriminant function analysis (DFA), linear discriminant analysis (LDA), cluster analysis, and nearest neighbor. Each possibility represents a separate embodiment of the present invention. In one embodiment, the at least one algorithm is discriminant function analysis (DFA).

In another aspect, the present invention provides a method of diagnosing, monitoring, prognosing or staging Parkinson's disease in a subject, the method comprising the steps of: (a) providing a system as disclosed herein; (b) exposing the at least one sensor to a test exhaled breath sample; (c) measuring at least one response induced parameter from the at least one sensor upon exposure to the test sample to obtain a response pattern; and (d) analyzing the response pattern obtained in step (c) using a learning and pattern recognition algorithm by comparing it to stored data obtained from a control sample whereby a significantly different response pattern of the test sample as compared the control sample is indicative of PD, as well as its stage.

In some embodiments, the method disclosed herein further provides the differentiation between healthy subjects, subjects having early-stage PD, and subjects having advanced-stage PD.

In another embodiment, the method of the present invention further comprises the step of concentrating the test exhaled breath sample prior to step (b) using at least one of a breath concentrator and a dehumidifying unit.

In certain embodiments, the response pattern is formed by the sensor detection of at least one volatile biomarker which is indicative of PD. In particular embodiments, the at least one volatile biomarker which is indicative of PD is selected from butylated hydroxytoluene, 1-methyl-3-(1-methylethyl)-benzene, styrene, 5-ethyl-2-methyl-octane, and ethylbenzene. Each possibility represents a separate embodiment of the present invention. In other embodiments, the at least one volatile biomarker which is indicative of PD is selected from methylene chloride, trichloromethane, di-n-octyl phthalate, 1,3-pentadiene and 1,2-benzenedicarboxylic acid. Each possibility represents a separate embodiment of the present invention. In further embodiments, the at least one volatile biomarker which is indicative of PD is selected from trichloroethylene, trichloromethane, 2,4-dimethyl-1-heptene, acetophenone, carbon disulfide, toluene and 2,4-dimethyl-heptane. Each possibility represents a separate embodiment of the present invention.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1A:
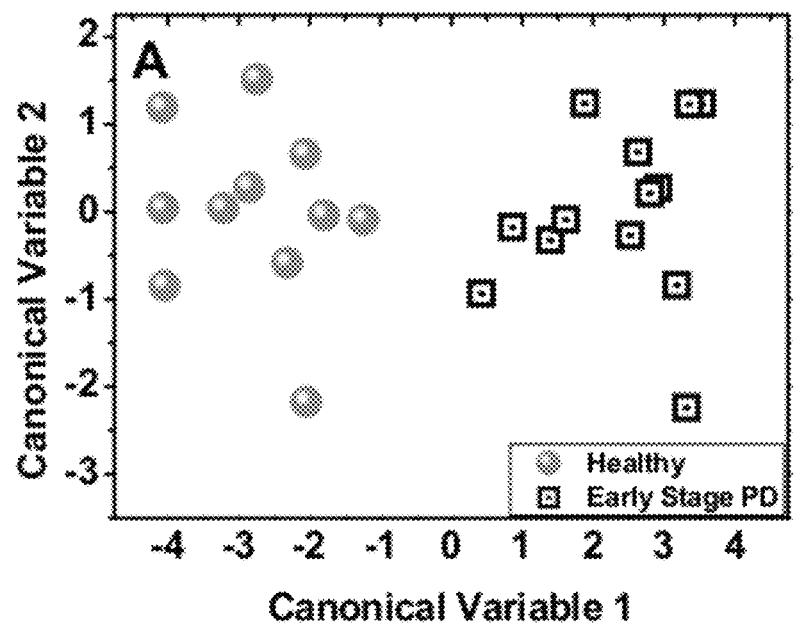
FIGS. 1A-1C. DFA plots of the first two canonical variables that were calculated from the responses of (1A) a sensor array comprising one sensor of coated carbon nanotubes, one sensor of coated spherical gold nanoparticles and one sensor of coated cubic platinum nanoparticles to distinguish early-stage PD patients (□) from healthy population (※) (1B) the same sensor array comprising the three sensors as described above to distinguish early-stage PD patient population (□) from late stage PD patient population (◇), and (1C) an extended sensor array comprising six sensors to distinguish early-stage patient population (□) and late-stage PD patient population (◇) from healthy population (※). Each point in the plot represents one patient.

The present invention provides a method of diagnosing, monitoring, prognosing or staging PD using at least one sensor comprising carbon nanotubes coated with cyclodextrin or derivatives thereof and/or at least one sensor comprising metal nanoparticles capped with an organic coating (e.g. mercapto derivatives). The invention further provides a method of distinguishing between healthy subjects and subjects having early-stage or advanced-stage PD.

The present invention provides a system which is suitable for the diagnosis, monitoring, prognosis or staging of PD. The system includes at least one chemically sensitive sensor as described herein, a detection means and a processing unit which utilizes a learning and pattern recognition algorithm to receive sensor output signals and compare them to stored data.

According to one embodiment, the at least one sensor comprises single-walled carbon nanotubes (SWCNTs) coated with cyclodextrin or cyclodextrin derivative wherein the nanotubes are arranged in a random network configuration. In some embodiments, the network of SWCNTs can be fabricated by a physical manipulation or in a self-assembly process. The term "self-assembly" as used herein refers to a process of the organization of molecules without intervening from an outside source. The self-assembly process occurs in a solution/solvent or directly on a solid-state substrate.

Main approaches for the synthesis of carbon nanotubes in accordance with the present invention include, but are not limited to, laser ablation of carbon, electric arc discharge of graphite rod, and chemical vapor deposition (CVD) of hydrocarbons. Among these approaches, CVD coupled with photolithography has been found to be the most versatile in the preparation of various carbon nanotube devices. In a CVD method, a transition metal catalyst is deposited on a substrate (e.g. silicon wafer) in the desired pattern, which may be fashioned using photolithography followed by etching. The silicon wafer having the catalyst deposits is then placed in a furnace in the presence of a vapor-phase mixture of, for example, xylene and ferrocene. Carbon nanotubes typically grow on the catalyst deposits in a direction normal to the substrate surface. Various carbon nanotube materials and devices are currently available from commercial sources.

Other CVD methods include the preparation of carbon nanotubes on silica ($SiO_2$) and silicon surfaces without using a transition metal catalyst. Accordingly, areas of silica are patterned on a silicon wafer, by photolithography and etching. Carbon nanotubes are then grown on the silica surfaces in a CVD or a plasma-enhanced CVD (PECVD) process. These methods provide the production of carbon nanotube bundles in various shapes.

The term "single walled carbon nanotubes" as used herein refers to a cylindrically shaped thin sheet of carbon atoms having a wall which is essentially composed of a single layer of carbon atoms which are organized in a hexagonal crystalline structure with a graphitic type of bonding. A nanotube is characterized by the length-to-diameter ratio. It is to be understood that the term "nanotubes" as used herein refers to structures in the nanometer as well as micrometer range.

According to various embodiments, the single-walled carbon nanotubes of the present invention have diameters ranging from about 0.6 nanometers (nm) to about 100 nm and lengths ranging from about 50 nm to about 10 millimeters (mm). More preferably, the single-walled carbon nanotubes have diameters ranging from about 0.7 nm to about 50 nm and lengths ranging from about ranging from about 250 nm to about 1 mm. Even more preferably, the single-walled carbon nanotubes have diameters ranging from about 0.8 nm to about 10 nm and lengths ranging from about 0.5 micrometer (μm) to about 100 μm. Most preferably, the single-walled carbon nanotubes of the present invention have diameters ranging from about 0.9 nm to about 5 nm and lengths ranging from about 1 μm to about 50 μm.

According to the principles of the present invention, the single walled carbon nanotubes are coated with cyclodextrin or a derivative thereof. Suitable cyclodextrin or derivative thereof include, but are not limited to, α-cyclodextrin, β-cyclodextrin, γ-cyclodextrin, methyl-β-cyclodextrin, 2,6-dibutyl-β-cyclodextrin, hydroxypropyl-β-cyclodextrin, 2,6-di-O-methyl-β-cyclodextrin, permethylated α-cyclodextrin-6$^A$-monoalcohol nitrate, dinitrophenyl substituted β-cyclodextrin-based chiral stationary phases, β- and γ-cyclodextrins bearing 4-amino-7-nitrobenz-2-oxa-1,3-diazole functional groups, sulfated and carboxy-methylated β-cyclodextrins, mono(6-cyclohexylamino-6-deoxy)-β-cyclodextrin, mono-(6-benzyl-imino-6-deoxy)-β-cyclodextrin, mono [6-(o-amino-phenyl)imino-6-deoxy]-β-cyclodextrin, mono [6-(p-aminophenyl)imino-6-deoxy]-β-cyclodextrin, mono [6-(α-naphthyl)imino-6-deoxy]-β-cyclodextrin, hexakis(6-O-benzoyl)-α-cyclodextrin, heptakis(2,3,6-tri-O-benzoyl)-β-cyclodextrin, heptakis(2,3,6-tri-β-methyl)-β-cyclodextrin, hexakis(6-O-benzoyl-2,3-di-O-benzyl)-α-cyclodextrin, hexakis(2,3-di-O-benzyl)-α-cyclodextrin, 2-6-amino-β-cyclodextrin, permethylated-β-cyclodextrin, 2A,3A-Alloepithio-2A,3A-dideoxy-β-cyclodextrin, and combinations thereof. Each possibility represents a separate embodiment of the present invention. Exemplary coatings include α-cyclodextrin, carboxy-methylated β-cyclodextrin, heptakis(2,3,6-tri-O-methyl)-β-cyclodextrin and combinations thereof. Each possibility represents a separate embodiment of the present invention.

According to some embodiments, the at least one sensor comprises nanoparticles comprising conductive metal cores which are capped with an organic coating. Suitable non-limiting examples of conductive metal cores include, but are not limited to, Au, Ag, Ni, Co, Pt, Pd, Cu, and Al nanoparticles. Each possibility represents a separate embodiment of the invention.

In one embodiment, the coating of the conductive nanoparticle cores comprises a monolayer or multilayers of organic compounds, wherein the organic compounds can be small molecules, monomers, oligomers or polymers. Each possibility represents a separate embodiment of the present invention. Suitable organic compounds include, but are not limited to, alkylthiols, e.g., alkylthiols with $C_3$-$C_{24}$ chains, arylthiols, alkylarylthiols, alkenyl thiols, alkynyl thiols, cycloalkyl thiols, heterocyclyl thiols, heteroaryl thiols, alkylthiolates, alkenyl thiolates, alkynyl thiolates, cycloalkyl thiolates, heterocyclyl thiolates, heteroaryl thiolates, ω-functionalized alkanethiolates, arenethiolates, (γ-mercaptopropyl)tri-methyloxysilane, dialkyl disulfides and combinations thereof. Each possibility represents a separate embodiment of the present invention. In particular embodiments, the organic coating of the metal nanoparticles comprises 3-mercapto-propionate. In other embodiments, the organic coating of the metal nanoparticles comprises 2-mercapto-benzoazole. In yet other embodiments, the organic coating of the metal nanoparticles comprises 11-mercapto-1-undecanol.

An "alkyl" group refers to a saturated aliphatic hydrocarbon, including straight-chain, branched-chain and cyclic alkyl groups. In one embodiment, the alkyl group has 1-12 carbons designated here as $C_1$-$C_{12}$-alkyl. In another embodiment, the alkyl group has 2-6 carbons designated here as $C_2$-$C_6$-alkyl. In another embodiment, the alkyl group has 2-4 carbons designated here as $C_2$-$C_4$-alkyl. In a currently preferred embodiment, the alkyl group has 3-24 carbons designated here as $C_3$-$C_{24}$ alkyl. The alkyl group may be unsubstituted or substituted by one or more groups selected from alcohol, ketone, aldehyde, halogen, carbonate, carboxylate, carboxylic acid, acyl, amido, amide, amine, imine, ester, ether, cyano, nitro, and azido. Each possibility represents a separate embodiment of the present invention.

A "cycloalkyl" group refers to a non-aromatic mono- or multicyclic ring system. In one embodiment, the cycloalkyl group has 3-10 carbon atoms. In another embodiment, the cycloalkyl group has 5-10 carbon atoms. Exemplary monocyclic cycloalkyl groups include cyclopentyl, cyclohexyl, cycloheptyl and the like. An alkylcycloalkyl is an alkyl group as defined herein bonded to a cycloalkyl group as defined herein. The cycloalkyl group can be unsubstituted or substituted with any one or more of the substituents defined above for alkyl.

An "alkenyl" group refers to an aliphatic hydrocarbon group containing at least one carbon-carbon double bond including straight-chain, branched-chain and cyclic alkenyl groups. In one embodiment, the alkenyl group has 2-8 carbon atoms (a $C_{2-8}$ alkenyl). In another embodiment, the alkenyl group has 2-4 carbon atoms in the chain (a $C_{2-4}$ alkenyl). Exemplary alkenyl groups include ethenyl, propenyl, n-butenyl, i-butenyl, 3-methylbut-2-enyl, n-pentenyl, heptenyl, octenyl, cyclohexyl-butenyl and decenyl. An alkylalkenyl is an alkyl group as defined herein bonded to an alkenyl group as defined herein. The alkenyl group can be unsubstituted or substituted through available carbon atoms with one or more groups defined hereinabove for alkyl.

An "alkynyl" group refers to an aliphatic hydrocarbon group containing at least one carbon-carbon triple bond including straight-chain and branched-chain. In one embodiment, the alkynyl group has 2-8 carbon atoms in the chain (a $C_{2-8}$ alkynyl). In another embodiment, the alkynyl group has 2-4 carbon atoms in the chain (a $C_{2-4}$ alkynyl). Exemplary alkynyl groups include ethynyl, propynyl, n-butynyl, 2-butynyl, 3-methylbutynyl, n-pentynyl, heptynyl, octynyl and decynyl. An alkylalkynyl is an alkyl group as defined herein bonded to an alkynyl group as defined herein. The alkynyl group can be unsubstituted or substituted through available carbon atoms with one or more groups defined hereinabove for alkyl.

An "aryl" group refers to an aromatic monocyclic or multicyclic ring system. In one embodiment, the aryl group has 6-10 carbon atoms. The aryl is optionally substituted with at least one "ring system substituents" and combinations thereof as defined herein. Exemplary aryl groups include phenyl or naphthyl. An alkylaryl is an alkyl group as defined herein bonded to an aryl group as defined herein. The aryl group can be unsubstituted or substituted through available carbon atoms with one or more groups defined hereinabove for alkyl.

A "heteroaryl" group refers to a heteroaromatic system containing at least one heteroatom ring wherein the atom is selected from nitrogen, sulfur and oxygen. The heteroaryl contains 5 or more ring atoms. The heteroaryl group can be monocyclic, bicyclic, tricyclic and the like. Also included in this definition are the benzoheterocyclic rings. Non-limiting examples of heteroaryls include thienyl, benzothienyl, 1-naphthothienyl, thianthrenyl, furyl, benzofuryl, pyrrolyl, imidazolyl, pyrazolyl, pyridyl, pyrazinyl, pyrimidinyl, pyridazinyl, indolyl, isoindolyl, indazolyl, purinyl, isoquinolyl, quinolyl, naphthyridinyl, quinoxalinyl, quinazolinyl, cinnolinyl, pteridinyl, carbolinyl, thiazolyl, oxazolyl, isothiazolyl, isoxazolyl and the like. The heteroaryl group can be unsubstituted or substituted through available atoms with one or more groups defined hereinabove for alkyl.

A "heterocyclic ring" or "heterocyclyl" group refers to five-membered to eight-membered rings that have 1 to 4 heteroatoms, such as oxygen, sulfur and/or in particular nitrogen. These five-membered to eight-membered rings can be saturated, fully unsaturated or partially unsaturated, with fully saturated rings being preferred. Exemplary heterocyclic rings include piperidinyl, pyrrolidinyl pyrrolinyl, pyrazolinyl, pyrazolidinyl, morpholinyl, thiomorpholinyl, pyranyl, thiopyranyl, piperazinyl, indolinyl, dihydrofuranyl, tetrahydrofuranyl, dihydrothiophenyl, tetrahydrothiophenyl, dihydropyranyl, tetrahydropyranyl, and the like. An alkylheterocyclyl is an alkyl group as defined herein bonded to a heterocyclyl group as defined herein. The heterocyclyl group can be unsubstituted or substituted through available atoms with one or more groups defined hereinabove for alkyl.

"Ring system substituents" refer to substituents attached to aromatic or non-aromatic ring systems including, but not limited to, H, halogen, haloalkyl, ($C_1$-$C_8$)alkyl, ($C_2$-$C_8$)alkenyl, ($C_2$-$C_8$)alkynyl, ($C_6$-$C_{10}$)aryl, alcohol, ketone, aldehyde, carbonate, carboxylate, carboxylic acid, acyl, amido, amide, amine, imine, ester, ether, cyano, nitro, azido, and the like. Each possibility represents a separate embodiment of the present invention.

Sensors comprising metal nanoparticles capped with various organic coatings can be synthesized as is known in the art, for example using the two-phase method (Brust et al., J. Chem. Soc. Chem. Commun., 1994, 801, 2) with some modifications (Hostetler et al., Langmuir, 1998, 14, 24). Capped gold nanoparticles can be synthesized by transferring $AuCl_4^-$ from aqueous $HAuCl_4.xH_2O$ solution to a toluene solution by the phase-transfer reagent TOAB. After isolating the organic phase, excess thiols are added to the solution. The mole ratio of thiol:$HAuCl_4.xH_2O$ can vary between 1:1 and 10:1, depending on the thiol used. This is performed in order to prepare mono-disperse solution of gold nanoparticles in average size of about 3.5-5 nm. Exemplary procedures include, but are not limited to, thiol:Au mole ratios of 10:1 and 1:1 for dodecanethiol and butanethiol-capped gold nanoparticles, respectively at an average size of 5 nm. After vigorous stirring of the solution, aqueous solution of reducing agent $NaBH_4$ in large excess is added. The reaction is constantly stirred at room temperature for at least 3 hours to produce a dark brown solution of the thiol-capped Au nanoparticles. The resulting solution is further subjected to solvent removal in a rotary evaporator followed by multiple washings using ethanol and toluene. Gold nanoparticles capped with 2-mercaptobenzoazole can be synthesized by ligand-exchange method from pre-prepared hexanethiol-capped gold nanoparticles. In a typical reaction, excess of thiol, 2-mercaptobenzoazole, is added to a solution of hexanethiol-capped gold nanoparticles in toluene. The solution is kept under constant stirring for few days in order to allow as much ligand conversion as possible. The nanoparticles are purified from free thiol ligands by repeated extractions. The metal nanoparticles may have any desirable morphology including, but not limited to, a cubic, a spherical, and a spheroidal morphology. Each possibility represents a separate embodiment of the invention.

The synthesized nanoparticles can then be assembled (e.g. by a self-assembly process) to produce a film of capped nanoparticles. The term "film", as used herein, corresponds to a configuration of well-arranged assembly of capped nanoparticles. 2D or 3D films of capped nanoparticles may also be used. Exemplary methods for obtaining well-ordered two or three dimensional assemblies of capped nanoparticles include, but are not limited to, i. Random deposition from solution of capped nanoparticles on solid surfaces. The deposition is performed by drop casting, spin coating, spray coating and other similar techniques.
 ii. Field-enhanced or molecular-interaction-induced deposition from solution of capped nanoparticles on solid surfaces.
 iii. Langmuir-Blodgett or Langmuir-Schaefer techniques. The substrate is vertically plunged through self-organized/well-ordered 2D monolayer of capped nanoparticles at the air-subphase interface, wherein the latter is being subsequently transferred onto it. Multiple plunging of the substrate through the 2D monolayer of capped nanoparticles at the air-subphase interface results in the fabrication of the 3D-ordered multilayers of capped nanoparticles.
 iv. Soft lithographic techniques, such as micro-contact printing (mCP), replica molding, micro-molding in capillaries (MIMIC), and micro-transfer molding (mTM). These methods are based on variations of self-assembly and replica molding of organic molecules and polymeric materials, for fabricating capped nanoparticles from nanometer-scale to a mesoscopic scale (Zhao et al., J. Mater. Chem., 1997, 7(7), 1069).
 v. Various combinations of Langmuir-Blodgett or Langmuir-Schaefer methods with soft lithographic techniques can be used to produce patterned Langmuir-Blodgett films of molecularly modified capped nanoparticles which are transferred onto solid substrates.
 vi. Printing on solid-state or flexible substrates using an inject printer designated for printed electronics. A solution containing the capped nanoparticles is used as a filling material (or "ink") of the printing head according to procedures well known in the art.

The sensors of the present invention can be configured as any one of the various types of electronic devices, including, but not limited to, capacitive sensors, resistive sensors, impedance sensors, field effect transistor sensors, and the like, or combinations thereof. Each possibility represents a separate embodiment of the invention.

In one embodiment, the system of the present invention comprises a single sensor. In alternative embodiments, the system of the present invention comprises a plurality of sensors (sensor array), for example between 2 and 6 sensors. In some embodiments, the sensor array comprises a sensor of single walled carbon nanotubes coated with cyclodextrin or a derivative thereof and/or a sensor of metal nanoparticles capped with an organic coating. In other embodiments, the sensor array comprises the combination of a sensor of single walled carbon nanotubes coated with cyclodextrin or a derivative thereof and a sensor of metal nanoparticles capped with an organic coating. In one embodiment, the sensor array comprises one sensor of carbon nanotubes coated with carboxy-methylated β-cyclodextrin, one sensor of spherical gold nanoparticles coated with 2-mercapto-benzoazole, and one sensor of cubic platinum nanoparticles coated with 11-mercapto-1-undecanol. In another embodiment, the sensor array comprises one sensor of carbon nanotubes coated with α-cyclodextrin, one sensor of carbon nanotubes coated with carboxy-methylated β-cyclodextrin, one sensor of carbon nanotubes coated with heptakis(2,3,6-tri-O-methyl)-β-cyclodextrin, one sensor of spherical gold nanoparticles coated with 2-mercapto-benzoazole, one sensor of spherical gold nanoparticles coated with 3-mercapto-propionate, and one sensor of cubic platinum nanoparticles coated with 11-mercapto-1-undecanol.

In certain embodiments, the sensors of the present invention comprise one or more conducting elements. The conducting elements may include a source and a drain electrode separated from one another by a source-drain gap.

The system disclosed herein may further comprise a gate electrode wherein the sensor signal may be indicative of a certain property (e.g. resistance) of the nanomaterial under the influence of a gate voltage. Alternatively, the sensor signal may be indicative of a capacitance property of the nanomaterial.

The sensor signal may be induced, according to the principles of the present invention by a change in any one or more of conductivity, resistance, impedance, capacitance, inductance, or optical properties of the sensor upon exposure to volatile biomarkers. Changes in the optical properties of the sensor network can be measured using e.g., spectroscopic ellipsometry.

The sensor signal is detected by a detection means. Suitable detection means include devices which are susceptible to a change in any one or more of resistance, conductance, alternating current (AC), frequency, capacitance, impedance, inductance, mobility, electrical potential, and an optical property and voltage threshold. Each possibility represents a separate embodiment of the present invention. In additional embodiments, the detection means includes devices which are susceptible to swelling or aggregation of nanomaterials as well as devices which are susceptible to a change in any one or more of optical signal, florescence, chemiluminsence, photophorescence, bending, surface acoustic wave, piezoelectricity and the like. Each possibility represents a separate embodiment of the present invention.

According to another embodiment, the present invention further provides a processing unit comprising a learning and pattern recognition analyzer, wherein the learning and pattern recognition analyzer receives sensor output signals and analyses them by various pattern analysis algorithms to produce an output signature. By comparing an unknown signature with a database of stored or known signatures, volatile biomarkers can be identified. The analyzer utilizes a learning and pattern recognition algorithm comprising artificial neural networks, such as multi-layer perception (MLP), generalized regression neural network (GRNN), fuzzy inference systems (FIS), self-organizing map (SOM), radial bias function (RBF), genetic algorithms (GAS), neuro-fuzzy systems (NFS), adaptive resonance theory (ART) and statistical methods such as principal component analysis (PCA), partial least squares (PLS), multiple linear regression (MLR), principal component regression (PCR), discriminant function analysis (DFA) including linear discriminant analysis (LDA), and cluster analysis including nearest neighbor. Each possibility represents a separate embodiment of the invention. In an exemplary embodiment, the algorithm used for processing the data is discriminant function analysis (DFA).

Additional algorithms suitable for identifying patterns of volatile biomarkers and quantifying their concentration include, but are not limited to, Fisher linear discriminant analysis (FLDA), soft independent modeling of class analogy (SIMCA), K-nearest neighbors (KNN), neural networks, genetic algorithms, and fuzzy logic algorithms. Each possibility represents a separate embodiment of the invention. In some embodiments, the Fisher linear discriminant analysis (FLDA) and canonical discriminant analysis (CDA) and combinations thereof are used to compare the output signature and the available data from the database. After analysis is completed, the resulting information can be displayed on a display or transmitted to a host computer.

The present invention further provides a method of diagnosing, monitoring, prognosing or staging PD in a subject using the system of the present invention. The at least one sensor is exposed to a test exhaled breath sample and at least one response induced parameter is measured by a detection means. The obtained signal is a response pattern which is preferably analyzed using a learning and pattern recognition algorithm by comparing it to stored data obtained from a control sample whereby a significantly different response pattern of the test sample as compared the control sample is indicative of PD, as well as its stage.

The term "significantly different" as used herein refers to a statistically significant quantitative difference between the pattern of the test sample and the pattern of a control sample. A statistically significant difference can be determined by any test known to the person skilled in the art. Common tests for statistical significance include, among others, t-test, ANOVA1 Kruskal-Wallis, Wilcoxon, Mann-Whitney and odds ratio. Individual samples (of unknown status) can be compared with negative control samples obtained from subjects which are not afflicted with PD. A statistically significant elevation or reduction in the particular response parameter being measured between the test and control sample qualifies as significant difference. A set of control samples can be stored as a reference collection for multiple analyses. In additional embodiments, where the staging of PD is desired, the unknown test sample may be compared to a sample obtained from a subject known to be afflicted with PD (positive control). In accordance with these embodiments, a significantly different response pattern of the test sample might be detected when the test sample of a subject with early-stage PD is compared to a control sample of a subject with advanced-stage PD and vice versa. In additional embodiments, the unknown test sample may be compared to a sample obtained from a subject known to be afflicted with Alzheimer's disease (AD). In accordance with these embodiments, the present invention provides a method for differentiating between healthy subjects, subjects having PD and subjects having AD. In further embodiments, the unknown test sample may be compared to a sample obtained from a subject known to be afflicted with Parkinsonism (also known as Parkinson-like disease or secondary PD). In accordance with these embodiments, the present invention provides a method for differentiating between subjects having PD and subjects having Parkinsonism.

The method of the present invention may further comprise the step of concentrating the test exhaled breath sample prior to the measurement using a breath concentrator and/or a dehumidifying unit.

Breath pre-concentrators that are within the scope of the present invention include, but are not limited to, I. Solid Phase Microextraction (SPME)—The SPME technique is based on a fiber coated with a liquid (polymer), a solid (sorbent), or combination thereof. The fiber coating extracts the compounds from the sample either by absorption (where the coating is liquid) or by adsorption (where the coating is solid). The SPME fiber is then inserted directly into the sensing apparatus for desorption and subsequent analysis (Ouyang, et al., *Anal. Bioanal. Chem.*, 2006, 386, 1059-1073; Coelho et al., *J. Chromatography B*, 2007, 853, 1-9).

II. Sorbent Tubes—Sorbent tubes are typically composed of glass and contain various types of solid adsorbent material (sorbents). Commonly used sorbents include activated charcoal, silica gel, and organic porous polymers such as Tenax and Amberlite XAD resins. Sorbent tubes are attached to air sampling pumps for sample collection. A pump with a calibrated flow rate in ml/min draws a predetermined volume of air through the sorbent tube. Chemicals are trapped onto the sorbent material throughout the sampling period. This technique was developed by the US National Institute for Occupational Safety and Health (NIOSH).

III. Cryogenic Condensates—Cryogenic condensation is a process that allows recovery of volatile compounds for reuse. The condensation process requires very low temperatures so that the volatile compounds can be condensed. Traditionally, chlorofluorocarbon (CFC) refrigerants have been used to induce condensation. Currently, liquid nitrogen is used in the cryogenic (less than $-160°$ C.) condensation process.

A dehumidifier that is within the scope of the present invention includes, but is not limited to, I. A device which draws moist air over cold refrigerated coils—using this approach, the air moisture condenses into droplets as it passes through cold refrigerated coils into a container. "Dried" air is then brought to its original temperature and returned to the sensing apparatus.

II. Silica Gel—is an amorphous form of silicon dioxide, which is synthetically produced in the form of hard irregular granules or beads. A microporous structure of interlocking cavities gives a very high surface area (800 square meters per gram). This unique structure renders the silica gel as a high capacity desiccant. Water molecules adhere to the surface of the silica gel due to its low vapor pressure as compared to the surrounding air. When pressure equilibrium is reached, the adsorption ceases. Thus, the higher the humidity of the surrounding air, the larger the amount of water that is adsorbed before equilibrium is reached. Silica gel is advantageous as a drying substance since the process of drying requires no chemical reaction and it produces no by products or side effects.

III. Activated carbon—is formed by processing charcoal to an extremely porous carbon substance. Due to its high degree of microporosity, the activated carbon possesses a very large surface area available for chemical reactions. Sufficient activation may be obtained solely from the high surface area, though further chemical treatments often enhance the adsorbing properties of the material.

IV. Desiccant Molecular Sieves—are synthetically produced, highly porous crystalline metal-alumino silicates. They are classified by the many internal cavities of precise diameters, namely, 3 Å, 4 Å, 5 Å, and 10 Å. Adsorption occurs only when molecules to be adsorbed have smaller diameters than the cavity openings. Molecules of high polarity are better adsorbed into the molecular sieves. Molecular sieves adsorb water molecules and other contaminants from liquids and gases down to very low levels of concentrations, often to 1 ppm.

The method of the present invention enables the detection of a single volatile biomarker as well as the detection of a plurality of volatile biomarkers and the unique pattern of these biomarkers which characterizes a particular stage of PD. In certain embodiments, the volatile biomarkers which are indicative of PD include, but are not limited to, at least one of butylated hydroxytoluene, 1-methyl-3-(1-methylethyl)-benzene, styrene, 5-ethyl-2-methyl-octane, and ethylbenzene. Each possibility represents a separate embodiment of the present invention. In other embodiments, the volatile biomarkers which are indicative of PD include, but are not limited to, at least one of methylene chloride, trichloromethane, di-n-octyl phthalate, 1,3-pentadiene and 1,2-benzenedicarboxylic acid. Each possibility represents a separate embodiment of the present invention. In further embodiments, the volatile biomarkers which are indicative of PD include, but are not limited to, at least one of trichloroethylene, trichloromethane, 2,4-dimethyl-1-heptene, acetophenone, carbon disulfide, toluene and 2,4-dimethyl-heptane. Each possibility represents a separate embodiment of the present invention The present invention encompasses the detection of breath biomarkers indicative of early-stage PD as well as breath biomarkers which are indicative of advanced-stage PD. Thus, according to the principles of the present invention, the discrimination between populations of healthy subjects, subjects having early-stage PD and subjects having advanced-stage PD is afforded by the present invention.

As used herein and in the appended claims the singular forms "a", "an," and "the" include plural references unless the content clearly dictates otherwise. Thus, for example, reference to "an organic coating" includes a plurality of such organic coatings and equivalents thereof known to those skilled in the art, and so forth.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Example 1

Test Population

The test population included 41 non-smoking volunteers (30 PD patients and 11 healthy controls) at the ages of 37-82. All volunteers were recruited from the out-patient population of the Department of Neurology and the Cognitive Unit, Rambam Health Care Campus (Haifa, Israel), and their accompanying persons. The PD patients were diagnosed in a specialist setting and staged according to the modified Hoen and Yahr (HY) scale (Hoehn et al., Neurology, 1967, 17, 427-442; Goetz et al., Mov. Disord., 2004, 19, 1020-1028). All PD patients were medicated (L-Dopa±agonists). A summary of the patient characteristics is provided in Table 1A and the full clinical details are provided in Table 1B.

TABLE 1A

Summary of the clinical characteristics of 41 non-smoking subjects that were tested in this study

| | Modified HY[1] stage | Stage Description[2] | Number of tested persons | sensors | GC-MS | Average Age +/− STD | Male: Female ratio |
|---|---|---|---|---|---|---|---|
| Early stage PD | 1 | Unilateral involvement only | 3 | 13 | 13 | 22 | 58 ± 9 | 7:6 |
| | 1.5 | Unilateral and axial involvement | — | | | | | |
| | 2 | Bilateral involvement without impairment of balance | 6 | | | | | |
| | 2.5 | Mild bilateral disease with recovery on pull test | 4 | | | | | |
| Adv. stage PD | 3 | Mild to moderate bilateral disease; some postural instability; physically independent | 14 | 17 | 17 | | 64 ± 10 | 10:7 |
| | 4 | Severe disability; still able to walk or stand unassisted | 3 | | | | | |
| | 5 | Wheelchair bound or bedridden unless aided | — | | | | | |
| Healthy controls | | | 11 | 11 | 9 | | 60 ± 7 | 4:7 |

[1]HY = Hoehn and Yahr

TABLE 1B

Clinical characteristics of 41 non-smoking subjects (13 early stage PD patients, 17 advanced stage PD patients and 11 healthy controls) at the ages of 37-82 which were tested in this study

| Category | Sub-Category | sensors | GC-MS | Stage | DBC | Age | Gender | Other diseases | Medication/Vitamins |
|---|---|---|---|---|---|---|---|---|---|
| PD | Early Stage PD | x | | 2.5 | | 58 | F | hypertension | PK-Merz, Pergolide, Azilect, Normiten, Cabaser, coenzyme Q10, vitamin C, Modafmil, Tritace COMP |
| | | x | x | 1 | | 58 | F | hypertension, Crohn's disease | PK-Merz, Requip, Dimitone, Dekinet, Tritace |
| | | x | | 2 | | 72 | M | hypertension | Dopicar, Requip, Donepezil, Convertin |
| | | x | x | 2.5 | | 37 | M | no | PK-Merz, Requip, Azilect |
| | | x | x | 2.5 | | 56 | F | hyperlipidemia, ischemic heart disease, post PTCA | Azilect, Norvasc, Sifrol, Disothiazide, Convertin, Micropirin, Simovil, Sifrol |
| | | x | x | 2.5 | | 59 | M | hypothyroidism | PK-Merz, Azilect, Stalevo, Eltroxin, Sifrol, Deralin |
| | | x | x | 2 | | 52 | F | depression | Requip, Azilect, Kemadrin, vitamin C, vitamin D coenzyme Q10, Viepax, Tricardia, Omega 3 |
| | | x | x | 2 | | 65 | F | hypertension, hyperlipidemia | Requip, Azilect, Vitamin D, Normiten, Disothiazide, Lipidal, Aspirin, Omega 3, PK-Merz |
| | | x | x | 1 | | 69 | M | n/a | Requip, Cabaser, Pramipexole, Dekinet, Dopicar, PK-Merz, Selegiline, Donepezil Exelon, Memox, Azilect |
| | | x | x | 1 | | 48 | M | hyperlipidemia | Requip, Cabaser, Pramipexole, Dekinet, Dopicar, PK- Merz, Selegiline, Donepezil Exelon, Memox, Azilect |
| | | x | x | 2 | n/a | 53 | M | diabetes, peptic ulcer, pemphigus, gout, sleep | Azilect, Kemadrin |

TABLE 1B-continued

Clinical characteristics of 41 non-smoking subjects (13 early stage PD patients, 17 advanced stage PD patients and 11 healthy controls) at the ages of 37-82 which were tested in this study

| Category | sensors | GC-MS | | | Age | Gender | Other diseases | Medication/Vitamins |
|---|---|---|---|---|---|---|---|---|
| | | | | | | | disturbance, hypertension, hyperlipidemia, osteoporosis | |
| | x | x | 2 | | 63 | F | hypercholesterolemia, hypothyroidism, smoker | Jumex, Eltroxin, Ezetrol |
| | x | | 2 | | 68 | M | sleep apnea | Sifrol, Remotiv |
| Advanced Stage PD | x | | 4 | x | 63 | F | hyperlipidemia, hypertension, depression, anxiety | Dopicar, PK-Merz, Lorivan, Lopresor, Amlow, Co-Diovan, Aspirin, Simovil, Vasodip, Pramipexole, Jumex, Alpralid, Evitol, Cipralex |
| | x | x | 3 | | 55 | F | no | Dopicar, PK-Merz, Kemadrin, Comtan, Lyrica, Motilium, Apo-go |
| | x | x | 4 | x | 56 | M | no | Dopicar, Lorivan |
| | x | x | 4 | | 70 | F | no | Evitol, Comtan, Dopicar, Requip, Sinemet Cr, Neurontin, folic acid, Jumex, Avilac |
| | x | x | 3 | | 82 | M | n/a | Cabaser, Pramipexole, Dekinet, Dopicar, PK-Merz, Selegiline, Donepezil, Exelon, Memox |
| | x | x | 3 | | 67 | M | hypertension, gastritis, celiac disease, Paget's disease, sleep apnea, hypertriglyceridemia | Stalevo, Sinemet CR, Requip, PK-Merz, Normiten, Micropirin, Lanton, Lyrica, Novitropan, Xatral |
| | x | x | 3 | | 72 | F | osteoporosis, mixed hyperlipidemia, s/p breast neoplasm | Stalevo, Simovil, Caltrate |
| | x | x | 3 | n/a | 72 | M | hyperlipidemia, Acute MI, PTCA, IHD, psoriasis, CVA | PK-Merz, Requip, Azilect, Stalevo, Kemadrin, Lopressor, Norvasc, Ocsaar, Ocsaar plus, Simovil, Cartia, Avilac |
| | x | x | 3 | n/a | 62 | F | no | Dopicar, PK-Merz, Requip, Azilect, Dekinet |
| | x | x | 3 | | 75 | M | IHD, osteoarthritis, S/P PTCA | Dopicar, Azilect, Requip |
| | x | x | 3 | n/a | 71 | F | mixed hyperlipidemia, headache | PK-Merz, Requip, Stalevo, Selegiline |
| | x | x | 3 | | 50 | F | hyperlipidemia, Iron def. anemia, nonalcoholic steatohepatitis, vitamin D deficiency, lumbar disc displacement, depressive disorder | Dopicar, PK-Merz, Azilect, Sinemet |
| | x | | 3 | | 72 | M | kidney stones, hyperlipidemia, Ischemic heart disease, osteoporosis | PK-Merz, Requip, Stalevo, Sinemet CR, Xatral, Clonex |
| | x | | 3 | x | 52 | M | no | Kemadrin, Remeron Motilium |
| | x | | 3 | | 60 | M | s/p perforation of ulcer, depression | Dopicar, PK-Merz, Requip |
| | x | | 3 | | 43 | M | depressive dis., sleep disturbance | Azilect, Seroxat, Kemadrin |
| | x | | 3 | | 67 | M | NIDDM, REM behavior disorder, hyperlipidemia, vitamin B12 deficiency | PK-Merz, Requip, Stalevo, Sinemet, Azilect |

| Category | sensors | GC-MS | Age | Gender | Other diseases | Medication/Vitamins |
|---|---|---|---|---|---|---|
| Healthy | x | | 58 | M | no | no |
| | x | x | 69 | F | hypertension, thyroidectomy | |

TABLE 1B-continued

Clinical characteristics of 41 non-smoking subjects (13 early stage PD patients, 17 advanced stage PD patients and 11 healthy controls) at the ages of 37-82 which were tested in this study

| | | Age | Gender | Conditions | Medications |
|---|---|---|---|---|---|
| x | x | 65 | F | hypertension, hypothyroidism, depression | Normiten, Eltroxin, Cipralex, Mega gluflex, Bondormin |
| x | x | 56 | M | no | Multi-vitamins |
| x | x | 55 | M | no | no |
| x | x | 57 | M | no | no |
| x | x | 56 | F | no | no |
| x | x | 73 | F | hypertension, hypercholesterolemia | Vascase plus, simovil |
| x | x | 52 | F | hypertension | Tritace, Disothiazide, Normiten, Norvasc |
| x | x | n/a | F | diabetes, hypercholesterolemia hypertension | Ezetrol, Empvil |
| x | | 51 | F | gastrisis, hypothyroidism | Eltroxin |

Ethical approval was obtained from the Rambam Healthcare Campus and Technion's committee for supervision of human experiments, Haifa, Israel. The clinical trial was registered at ClinicalTrials.gov (registration no.: NCT01246336). The volunteers gave their written informed consent prior to the breath collection, and all experiments were performed according to the guidelines of the Rambam Healthcare Campus and Technion's committee for supervision of human experiments.

Example 2

Clinical Study

The clinical study was cross-sectional. Highly accurate diagnosis was achieved through clinical examination in a specialist setting. The clinical diagnosis was used as a reference standard. The tested PD patients were divided into two groups, namely early stage and advanced stage PD. These two patient groups were compared with healthy controls. 13 PD patients that were classified as stages 1, 2 and 2.5 on the modified Hoehn and Yahr scale were grouped as early stage PD patients, and 17 patients that were classified as stages 3 and 4 were grouped as advanced stage PD patients. Signal patterns of the three test groups were obtained using the system of the present invention as follows: (i) early stage PD patients were compared to healthy controls, (ii) advanced stage PD patients were compared to early stage PD patients, and (iii) all three test groups (early stage PD, advanced stage PD and healthy controls) were analyzed together. No patient exclusion criteria were applied after recruitment. Noteworthy that the three test groups were age matched, but differed in their gender-ratio. This relaxation of the recruiting criteria is acceptable, since the sensors of the present invention have been specially tailored to show little sensitivity to confounding factors such as gender (cf. Peng et al., Br. J. Cancer, 2010, 103, 542).

Example 3

Breath Collection

Exhaled alveolar breath was collected in a controlled manner from PD patients and from healthy controls in the hospital environment. The inhaled air was cleared of ambient contaminants by repeatedly inhaling to total lung capacity for 3-5 minutes through a mouthpiece (purchased from Eco Medics, Duerten, Switzerland) that contained a filter cartridge on the inspiratory port, thus greatly reducing the concentration of exogenous volatile organic compounds and removing 99.99% of the exogenous compounds from the air during inspiration. The unfiltered hospital air was sampled for typical hospital contaminations (Amann et al., Euro. Resp. Soc. Monograph, 2010, 49, 96). The following typical hospital contaminants: 2-methyl-2-propanol, ethanol and methylisobutyl-ketone, were detected using GC-MS in conjugation with Solid-Phase Micro-Extraction (SPME). Trace amounts of these compounds were identified in less than 23% of the study population, indicating that the air filtration was efficient. Immediately after lung washout, subjects exhaled through a separate exhalation port of the mouthpiece against 10-15 cm $H_2O$ pressure to ensure closure of the vellum so that nasal entrainment of gas was excluded. The dead space air was automatically filled into a separate bag and the alveolar breath into a 750 ml Mylar sampling bag (purchased from Eco Medics) in a single-step process that did not require the subject undertaking the test to change between the dead space and alveolar breath bags. The Mylar bags were re-used and thoroughly cleaned before each use with flowing $N_2$ (99.999% purity) gas for 5-8 minutes. Notably, GC-MS in conjugation with Solid-Phase Micro-Extraction (SPME) has shown that this purification process eliminates 98% of contaminants and/or volatile biomarkers from the previous sample tested in a specific Mylar bag. 1-2 bags were collected per test subject for analysis with GC-MS and/or for analysis with the sensors of the present invention. All bags were analyzed within 7 days from the time of breath collection, much before the allowed 3-weeks storage period, after which the samples might start to deteriorate (Peng et al., Nature Nanotech., 2009, 4, 669; Peng et al., Br. J. Cancer, 2010, 103, 542; Peng et al., Nano Lett., 2008, 8, 3631).

Example 4

Sensor Breath Analysis

The breath samples were tested using individual sensors and a plurality of sensors (sensor array) as described herein. The array contained six sensors as follows: three sensors of random networks of single-walled carbon nanotubes (RN-CNTs) that were functionalized with layers of different cyclodextrin (CD) derivatives, 2 sensors of spherical gold (Au) nanoparticles with different organic coatings, and 1 sensor based on organically functionalized cubic platinum (Pt)

nanoparticles. The base materials and organic functionalities of the sensors are listed in Table 2. The sensor fabrication was performed as described in Peng et al., Nano Lett., 2008, 8, 3631; Dovgolevsky et al., Small, 2008, 4, 2059; Dovgolevsky et al., Small 2009, 5, 1158; and Haick et al., ACS Nano 2009, 3, 1258; the contents of each of these references are hereby incorporated by reference. Each sensor showed a characteristic response to all (or to a certain subset) of the volatile biomarkers which were found in the exhaled breath samples.

discriminated are defined before the analysis is performed. DFA determines the linear combinations of the sensor values such that the variance within each class is minimized and the variance between classes is maximized. The DFA output variables (viz. canonical variables) are obtained in mutually orthogonal dimensions. The first canonical variable is the most powerful discriminating dimension, but the following canonical variables might also represent additional dimensions of differentiation. Thus, DFA effectively reduces the

TABLE 2

Base materials and organic functionalities of the sensors

| Sensor no. | Base material | Organic functionality | Healthy - Early PD - Late PD | Healthy - Early PD | Early PD - Late PD |
|---|---|---|---|---|---|
| 1 | CNTs | α-CD | x | | |
| 2 | | Carboxy-methylated β-CD | x | x | x |
| 3 | | Heptakis(2,3,6-tri-O-methyl)-β-CD | x | | |
| 4 | Au NPs | 2-Mercapto-benzoazole | x | x | x |
| 5 | | 3-Mercapto-propionate | x | | |
| 6 | Pt NPs | 11-Mercapto-1-undecanol | x | x | x |

CNT: carbon nanotubes;
NPs: nanoparticles;
CD = cyclodextrin

Example 5

GC-MS Breath Analysis

The constituent volatile biomarkers of the collected breath were identified using GC-MS (GC-6890N; MS-5975; Agilent Technologies Ltd). The GC-MS analysis was preceded by SPME for pre-concentrating the volatile biomarkers in the breath samples as follows: A manual SPME holder with an extraction fiber was inserted into the Mylar bag for 30 minutes before being delivered to the GC-MS. Fibers with polydimethylsiloxane-divinylbenzene (coating obtained from Sigma-Aldrich) were used. The extracted fiber in the manual SPME holder was inserted into the injector of the GC (splitless mode). The following oven profile was used: 10 min at 35° C., 7.5° C. per min to 130° C., 13° C. per min to 290° C., 1 min at 290° C. A capillary column SLB-5MS low phenyl methyl siloxane content (30 m length, 0.25 mm internal diameter, 0.50 µm thickness, from Sigma-Aldrich) was used. The column pressure was set at 8.22 PSI, and the initial flow rate was 1.0 ml per min. The identification of the volatile biomarkers was performed by a spectral library match using the retention time. The volatile biomarkers common for >75% of the healthy and/or PD samples, as well as their abundance with experimental error (standard error, SE), were identified using the Automated Mass Spectral Deconvolution and Identification System (AMDIS) software.

Example 6

Statistical Analysis

The signals from the sensor array were analyzed using discriminant factor analysis (DFA; Ionescu et al., Analyst, 2002, 127, 1237; Brereton, Chemometrics, Application of Mathematics Statistics to Laboratory Systems, Chichester, Ellis Horwood, 1990). Four features were read out per each sensor. The features are indicative of the normalized resistance change after exposure to the breath samples and of the area under the time evolution curve of the sensor's resistance (in the middle and at the end of the signal). DFA is a linear, supervised pattern recognition method. The classes to be multidimensional experimental data, improves the human perception of the data and allows the distinction of clusters through visual perception of the first or the first and second canonical variables. The classification success rate of the binary problems was estimated through leave-one-out cross validation. All possibilities of leaving out one sample were tested and the left out sample was classified as true positive (TP), true negative (TN), false positive (FP) and false negative (FN), using standard cluster analysis.

Example 7

GC-MS Breath Analysis

Gas-chromatography/mass-spectrometry (GCMS-QP2010; Shimadzu Corporation, Japan) combined with a thermal desorption system (TD20; Shimadzu Corporation, Japan) was used for the chemical analysis of the breath samples. A Tenax TA adsorbent tube (Sigma Aldrich Ltd.) was employed for pre-concentrating the volatile organic compounds (VOCs) in the breath samples. Using a custom made pump system, the breath samples from the Mylar bags were sucked through the TA tube at 100 mL/min flow rate, being then transferred to a thermal desorption (TD) tube (Sigma Aldrich Ltd.) prior to GC-MS analysis. The following oven temperature profile was set: (a) 10 min at 35° C.; (b) 4° C./min ramp to 150° C.; (c) 10° C./min ramp to 300° C.; and (d) 15 min at 300° C. An SLB-5 ms capillary column (Sigma Aldrich Ltd.) with 5% phenyl methyl siloxane (30 m length, 0.25 mm internal diameter, and 0.5 µm thickness) was employed. The splitless injection mode was used for 2 min, at 30 cm/s constant linear speed and 0.70 mL/min column flow. GC-MS chromatogram analysis was realized using the GCMS solutions version 2.53SU1 Postrun analysis program (Shimadzu Corporation) and by XCMS software algorithms. Both T-Test and non-parametric Wilcoxon tests were used to determine statistical differences of the VOCs' abundance between the research groups.

Results:

Identification of Early-Stage PD and Monitoring of Disease Progression Using the Sensors/Sensor Array of the Present Invention The breath samples of 17 advanced-stage PD patients, 13 early-stage PD patients and 11 healthy controls were analyzed using a sensor array with six tailor-made nano-sensors (Example 4; Table 2). In addition, the analysis was performed using each of these sensors alone. The multi-dimensional response was analyzed using DFA. Based on the clinical evaluation, the patients were staged using the widely used modified HY scale. The differentiation between early and advanced stage PD was based on the modified HY staging, as shown in Table 1. However, the HY scale mixes impairment and disability in rather broad categories and progression between the different stags is not linear. Thus, it is difficult to draw the line between early stage and advanced stage PD. Stages 1 and 2 clearly depict mild and early PD, and stage 4 defines advanced disease. Stage 3 is more ambiguous since the hallmark of stage 3, namely the occurrence of balance difficulties, has never been defined in a standardized manner and no systematic application of the objective pull test and teaching tape has been developed. In this study, stages 3 and 4 were grouped together as advanced disease.

Figure 1B:
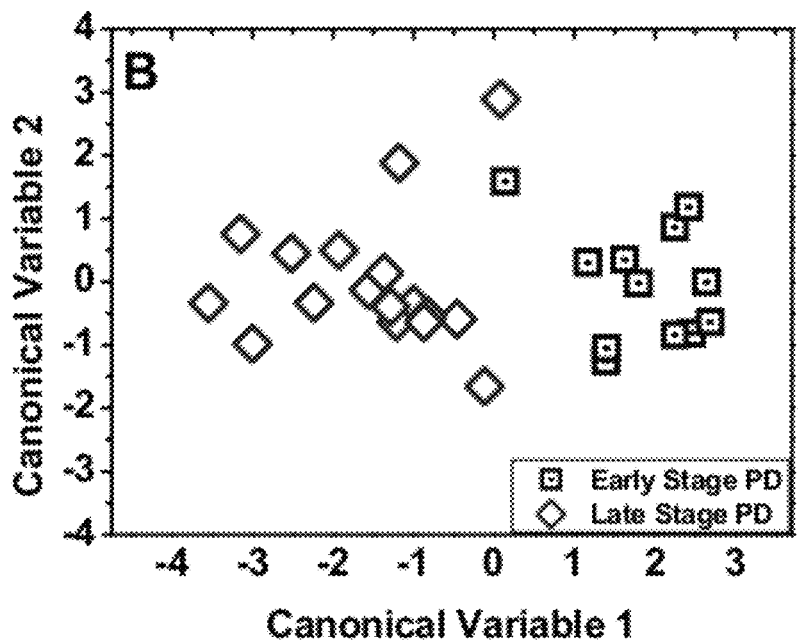
Figure 1C:
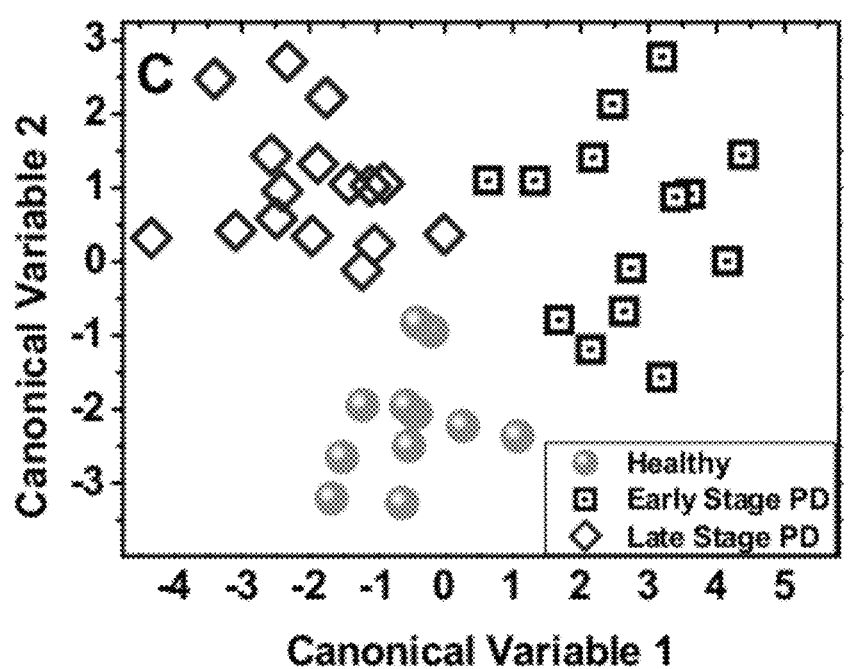

The feasibility of the sensors/sensor array in diagnosing early stage PD disease was tested. Early stage PD states and healthy states could be distinguished based on the signals of each the three sensors listed in Table 2 (second column from the right) as well as an array comprising the three sensors. The number of input parameters was kept low enough to avoid over-fitting during the DFA. FIG. 1A shows the analysis using an array of three sensors (Table 2). Two distinct clusters, corresponding to the two test groups, can be observed in CV space. Thus, early stage PD patients are completely distinguished from healthy controls along the axis of the first canonical variable, with positive values for the former and negative values for the latter. The classification success rate was estimated through leave-one-out cross validation and the results (correct and false classifications) are represented in Table 3A. The sensitivity, specificity and accuracy of the classification were determined as 100%, 91%, and 96%, respectively. Next, the ability of the sensor array to monitor disease progression was tested. Early stage and advanced PD states were distinguished using the same three sensors that were used for the identification of early stage PD. FIG. 1B shows that excellent separation of the two groups can be observed again along the first canonical variable. The sensitivity, specificity and accuracy of identification of disease progression were determined as 82%, 77%, and 80%, respectively (Table 3B). When using each of these sensors alone, the sensitivity, specificity and accuracy of the classification were determined as 60%, 62%, and 61%, respectively. Thus, the sensitivity and specificity for the detection of early stage PD and disease progression as demonstrated herein provides the classification of the disease stages using each of the sensors of the present invention. FIG. 1C shows that all three test groups can be clearly distinguished in the same analysis using an array of six sensors (Table 2). Noteworthy, that the second canonical variable represents a considerable dimension of differentiation. The use of more input parameters is permissible, because of the increased total number of samples. The clusters in FIGS. 1A-1C appear differently in canonical variable space, because the input data for the statistical algorithm is different.

TABLE 3A&B

Evaluation of the classification using the leave-one-out cross validation (A)

|  | Classified as early-stage PD | Classified as healthy |
|---|---|---|
| Early-stage PD | 13 | 0 |
| healthy | 1 | 10 |

(B)

|  | Classified as advanced-stage PD | Classified as early-stage PD |
|---|---|---|
| Advanced-stage PD | 14 | 3 |
| Early-stage PD | 3 | 10 |

Identification of Volatile PD Biomarkers in Exhaled Breath

The chemical composition of the exhaled breath of PD patients was analyzed and compared to the breath of healthy controls in order to glean information regarding the volatile biomarkers which are indicative of PD. A representative subset of the collected breath samples were analyzed (21 PD and 9 healthy controls, see Table 1) using GC-MS in combination with SPME as described in Example 5 hereinabove. The PD samples were grouped together into a single class because of the small sample size and the large experimental scatter between the samples. The abundance of certain substances was found to be different for the two study groups, i.e. certain differences in the average chemical composition of the breath was found. Without being bound by any theory or mechanism of action, these differences could account for the differences in the observed patterns as detected by the sensors. Five substances that differ in average abundance in breath samples from PD patients as compared to healthy controls may be used as volatile biomarkers for PD.

Figure 2:
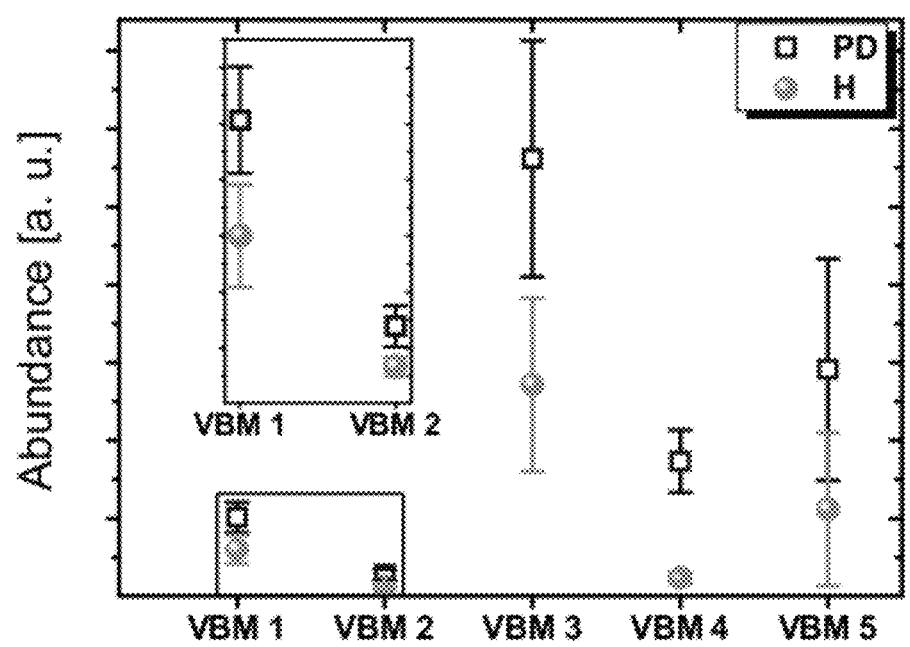
FIG. 2. Abundance of five volatile biomarkers (VBMs) that were found in the breath of >75% of PD patients (□) and >75% of healthy controls (H; ※). The symbols represent the average abundance and the error bars mark the borders of the 90% CIs.

FIG. 2 shows the volatile biomarkers that (i) were present in >75% of the PD patients and >75% of the healthy controls and (ii) that showed no (or little) overlap in average abundance (with 90% confidence interval, CI=1.65×SE). The comparison between the different populations was based on compound masses and retention times. The identification of the volatile biomarkers (VBMs) based on a p-xylene reference is as follows: VBM 1:butylated hydroxytoluene (m/z=205; retention time=36 s); VBM 2=1-methyl-3-(1-methylethyl)-benzene (m/z=119, retention time=21 s); VBM 3=styrene (m/z=104; retention time=16 s); VBM 4=5-ethyl-2-methyl-octane (m/z=43; retention time=21 s); and VBM 5=ethylbenzene (m/z=91; retention time=15 s). Noteworthy, m/z indicates the major target mass. The substances which were identified in the unfiltered hospital air as typical hospital contaminants (2-methyl-2-propanol, ethanol and methyl-isobutyl-ketone) were disregarded. The discriminative abilities of the sensor array are superior to those of GC-MS, even when preceded by SPME. Thus, the sensor array of the present invention provides the diagnosis and monitoring of PD at different stages suitable for general practitioners in non-specialist settings to allow the early diagnosis of new PD patients and monitoring of the disease progression and efficacy of treatment.

Figure 3:
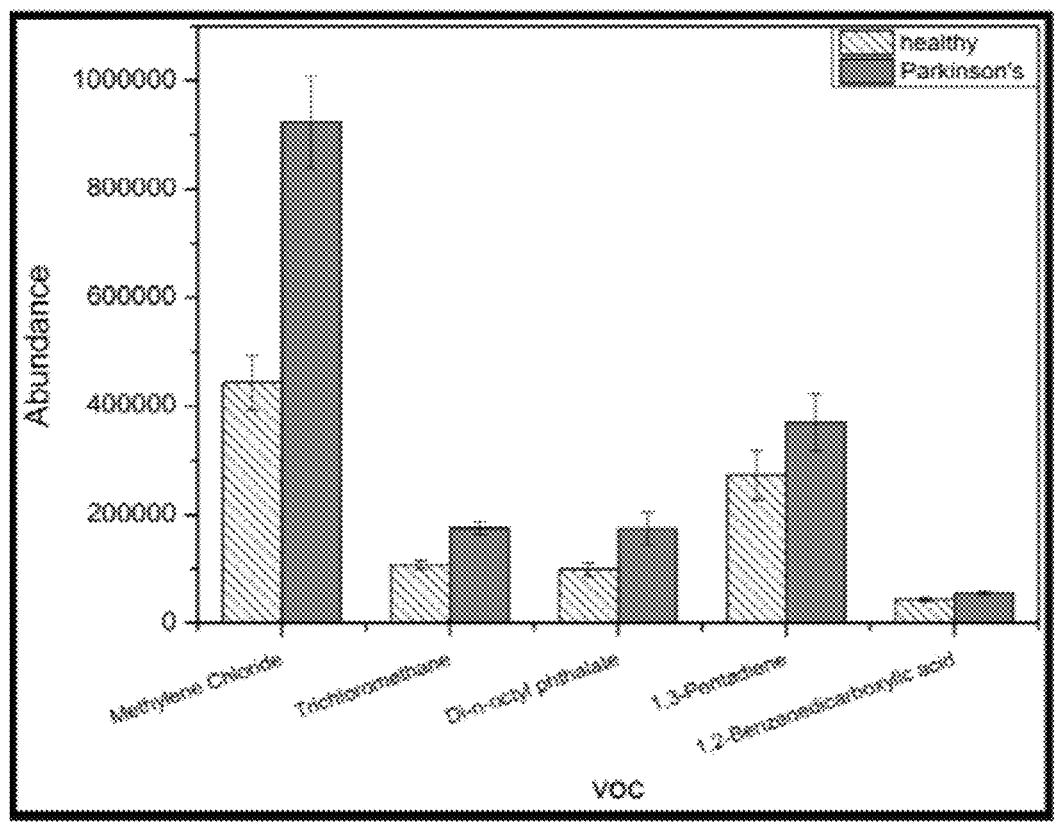
FIG. 3. Abundance of five volatile organic compounds (VOCs) which were found to be more abundant ($P<0.05$) among Parkinson's patients as compared to healthy subjects. The data represents the mean values±the standard errors.

In order to identify PD biomarkers, an additional GC-MS breath analysis was performed as described in Example 7 hereinabove. Five different volatile organic compounds (VOCs) were found significantly ($P<0.05$) more abundant in PD patients (n=15) than in healthy controls (n=9). FIG. 3 shows the VOC abundance of the five PD biomarkers: methylene chloride, trichloromethane, di-n-octyl phthalate, 1,3- pentadiene and 1,2-benzenedicarboxylic acid. These VOCs can therefore be used to diagnose and monitor PD patients.

Idiopathic Parkinson and Parkinson-like disease (Parkinsonism, also known as secondary PD) are prevalent degenerative disorders of the central nervous system. The diagnosis and the differentiation between the two disorders relies mostly on clinical symptoms. Usually patients of both groups have a very similar clinical presentation. When diagnosis is performed by a non-neurological specialist, misdiagnosis is very common (Michell et al., Metabolomics, 2008, 4, 191).

Figure 4A:
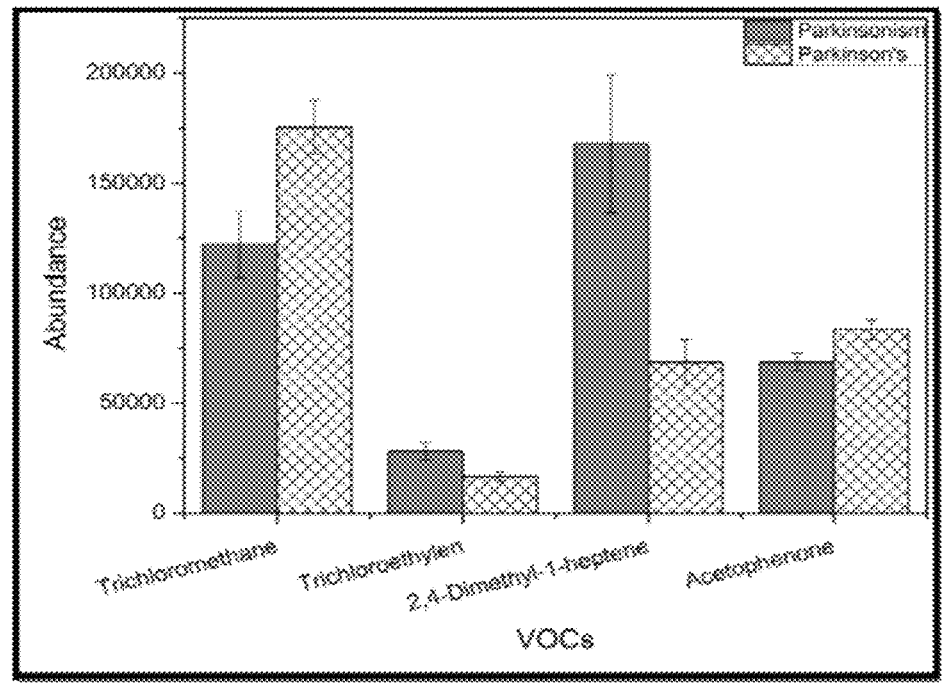
FIGS. 4A-4B. Abundance of seven VOCs which were found to be significantly different ($P<0.05$) in Parkinson's patients as compared to patients having Parkinsonism. The data represents the mean values±the standard errors.
Figure 4B:
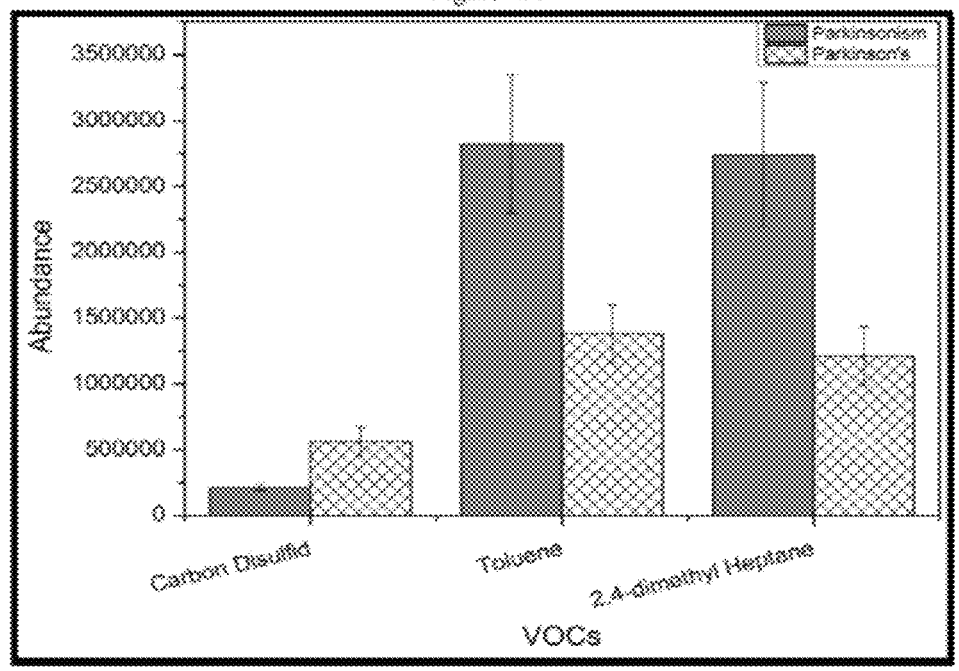

Results of chemical analysis of 15 PD patients, 6 Parkinson-like disease patients and 9 healthy subjects using GC-MS are shown in FIGS. 4A-4B. Seven different VOCs, including trichloroethylene, trichloromethane, 2,4-dimethyl-1-heptene, acetophenone, carbon disulfide, toluene and 2,4-dimethyl-heptane showed valid differences (P<0.05) between Parkinsonism and PD. These VOCs can therefore be used to diagnose and monitor PD patients and to differentiate PD patients from Parkinsonism.

Sensing Breath Samples of PD Vs. Alzheimer's Disease (AD) Patients

Figure 5A:
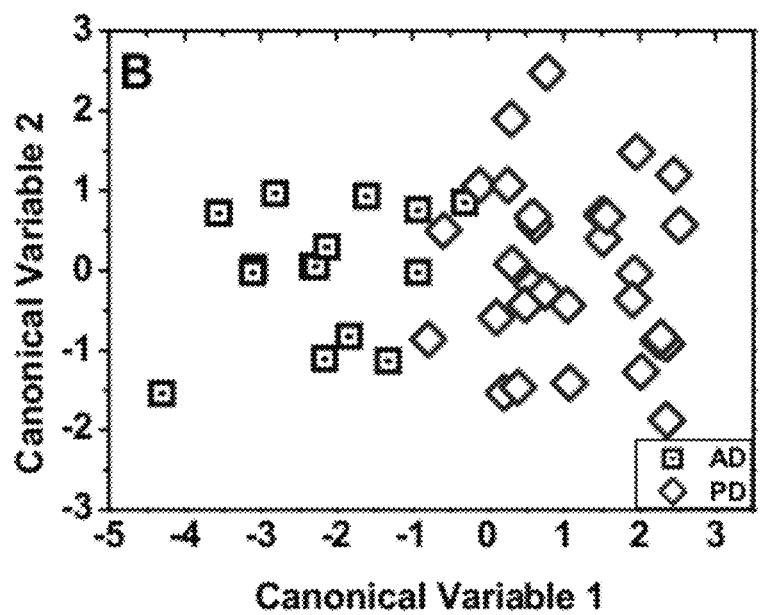
FIGS. 5A-5B. DFA plots of the first two canonical variables that were calculated from the responses of (5A) three sensors to breath samples of PD (◇) and AD (□) patient populations, and (5B) an extended array of six sensors to breath samples of PD (◇) and AD (□) patients and healthy controls (※). Each patient is represented by 1 point in the plot.
Figure 5B:
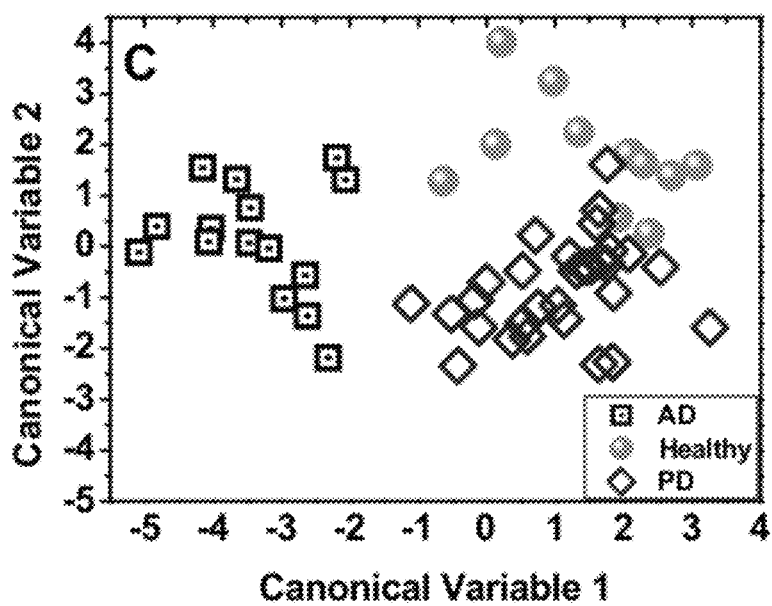

In order to provide the diagnosis and prognosis of PD suitable for clinical use, the diagnosis of PD should be distinguishable from the diagnosis of other neurodegenerative diseases such as Alzheimer's disease (AD), since patients of AD often suffer from clinical symptoms that are similar to those of PD patients. This may sometimes lead to the false diagnosis of either one of these diseases. The breath samples of 15 AD patients (ages 68±10, male:female ratio 7:8), 12 healthy controls and 30 PD patients were analyzed using the following sensor array: Two sensors based on random network of single walled CNTs functionalized with β-cyclodextrin (β-CD) and hydroxypropyl-β-CD and one sensor based on spherical Au nanoparticles coated with 3-mercapto-propionate. Four features (response induced parameters) were read out per sensor that relate to the normalized resistance change after exposure to the breath samples in the middle and at the end of the signal. The classification success rate of the binary problems was estimated through leave-one-out cross validation. For this purpose, DFA was computed using a training data set that excluded one test sample. After the DFA computation, the test sample was projected onto the two-dimensional DFA space, defined by the first two canonical variables (CV1 and CV2) that were calculated using the training set. Thereby, the test sample was "blinded" against the DFA model so that its class affiliation was unknown. All possibilities of leaving out one sample were tested and the left out sample was classified as true positive (TP), true negative (TN), false positive (FP) and false negative (FN), using standard cluster analysis. During the statistical analysis of the sensor signals, the number of DFA input parameters was kept low enough to avoid over-fitting. FIG. 5A shows that very good separation of AD and PD patients could be achieved along the first canonical variable. The classification success rate was estimated through leave-one-out cross validation and the results are summarized in Table 4. The sensitivity, specificity and accuracy of the classification of PD versus the AD control group were determined as 65%, 58%, and 61%, respectively. Thus, the sensors of the present invention provide the diagnosis of PD with excellent sensitivity and specificity to afford the differentiation of PD patients from AD patients. A further comparison of three test groups (PD patients, AD patients and healthy controls) was performed using an extended sensor array with six nano-sensors: Four sensors based on random network of single walled CNTs functionalized with β-cyclodextrin (β-CD), carboxy-methylated β-CD, hydroxypropyl-β-CD and heptakis(2,3,6-tri-O-methyl)-β-CD and two sensors based on spherical Au nanoparticles coated with 2-mercapto-benzoazole and 3-mercapto-propionate. FIG. 5B shows that all three test groups (PD, AD and healthy) could be distinguished in the same DFA plot. Noteworthy that the second canonical variable represents a considerable dimension of differentiation and that a larger overlap is observed between the PD group and the healthy group. The use of more input parameters is permissible, because of the increased total number of samples. The clusters in FIGS. 5A and 5B appear differently in canonical variable space, because the DFA input data is different.

TABLE 4

Classification success, estimated using the leave-one-out cross validation

|    | Classified as AD | Classified as PD |
|----|------------------|------------------|
| AD | 12               | 3                |
| PD | 4                | 26               |

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

The invention claimed is:

1. A system for diagnosing, monitoring, prognosing or staging Parkinson's disease, the system comprising:
   (a) an apparatus comprising at least one sensor comprising nanomaterials selected from the group consisting of single walled carbon nanotubes (SWCNTs) coated with α-cyclodextrin, SWCNTs coated with carboxy-methylated β-cyclodextrin, SWCNTs coated with heptakis(2, 3,6-tri-O-methyl)-β-cyclodextrin, Au nanoparticles capped with 3-mercapto-propionate, Au nanoparticles capped with 2-mercapto-benzoazole and Pt nanoparticles capped with 11-mercapto-1-undecanol, wherein the at least one sensor is configured to detect at least one volatile biomarker in a breath sample, which is indicative of Parkinson's disease, wherein said volatile biomarker is selected from the group consisting of butylated hydroxytoluene, 1-methyl-3-(1-methylethyl)-benzene, styrene, 5-ethyl-2-methyl-octane, and ethylbenzene; from the group consisting of methylene chloride, trichloromethane, di-n-octyl phthalate, 1,3-pentadiene and 1,2-benzenedicarboxylic acid; or from the group consisting of trichloroethylene, trichloromethane, 2,4-dimethyl-1-heptene, acetophenone, carbon disulfide, toluene and 2A-dimethyl heptane;
   (b) a processing unit comprising a learning and pattern recognition analyzer wherein the learning and pattern recognition analyzer receives sensor output signals and compares them to stored data; and
   (c) a reporting unit that provides a quantitative signal for the at least one volatile biomarker in the breath sample.

2. The system of claim 1, wherein the apparatus further comprises a sensor comprising SWCNTs coated with cyclodextrin selected from the group consisting of β-cyclodextrin, γ-cyclodextrin, methyl-β-cyclodextrin, 2,6-dibutyl-β-cyclodextrin, hydroxypropyl-β-cyclodextrin, 2,6-di-O-methyl-β-cyclodextrin, permethylated α-cyclodextrin-6$^4$-monoalcohol nitrate, dinitrophenyl substituted β-cyclodextrin-based chiral stationary phases, β- and γ-cyclodextrins bearing 4-amino-7-nitrobenz-2-oxa-1,3-diazole functional groups, sulfated β-cyclodextrin, mono-(6-cyclohexylamino-6-deoxy)-β-cyclodextrin, mono-(6-benzyl-imino-6-deoxy)-β-cyclodextrin, mono[6-(o-amino-phenyl)imino-6-deoxy]-β-cyclodextrin, mono[6-(p-aminophenyl)imino-6-deoxy]-β-cyclodextrin, mono[6-(α-naphthyl)imino-6-deoxy]-β-cyclodextrin, hexakis(6-O-benzoyl)-α-cyclodextrin, heptakis(2,3,6-tri-O-benzoyl)-β-cyclodextrin, hexakis(6-O-benzoyl-2,3-di-O-benzyl)-α-cyclodextrin, hexakis(2,3-di-O-benzyl)-α-cyclodextrin, 2-6-amino-β-cyclodextrin, permethylated-β-cyclodextrin, 2A,3A-Alloepithio-2A,3A-dideoxy-β-cyclodextrin, and combinations thereof.

3. The system of claim 1, wherein the single walled carbon nanotubes are organized in a random network configuration.

4. The system of claim 1, wherein the apparatus further comprises a sensor comprising metal nanoparticles capped with an organic coating, wherein the metal nanoparticles are selected from the group consisting of Au, Ag, Ni, Co, Pt, Pd, Cu, and Al nanoparticles.

5. The system of claim 4, wherein the organic coating of the metal nanoparticles comprises compounds selected from the group consisting of alkylthiols, arylthiols, alkylarylthiols, alkylthiolates, w-functionalized alkanethiolates, arenethiolates, (γ-mercaptopropyl)tri-methyloxysilane, dialkyl disulfides and combinations thereof.

6. The system of claim 1, wherein the Au and/or Pt nanoparticles have a morphology selected from a cubic, a spherical, and a spheroidal morphology.

7. The system of claim 1, wherein the at least one sensor is configured in a form selected from the group consisting of a capacitive sensor, a resistive sensor, an impedance sensor, and a field effect transistor sensor.

8. The system of claim 1 comprising a single sensor.

9. The system of claim 1 comprising a plurality of sensors.

10. The system of claim 1, further comprising a detection device that measures changes in at least one property of the at least one sensor, wherein the detection device is selected from the group consisting of a resistance measurement device, a conductance measurement device, an alternating current (AC) measurement device, a frequency measurement device, a capacitance measurement device, an impedance measurement device, an inductance measurement device, a mobility measurement device, an electrical potential measurement device, an optical property measurement device, a voltage threshold measurement device, a fluorescence measurement device, a chemiluminescence measurement device, a phosphorescence measurement device, a bending measurement device, a surface acoustic wave measurement device, and a piezoelectricity measurement device.

11. The system of claim 1, wherein the learning and pattern recognition analyzer comprises at least one algorithm selected from the group consisting of artificial neural network algorithms, principal component analysis (PCA), multi-layer perception (MLP), generalized regression neural network (GRNN), fuzzy inference systems (FIS), self-organizing map (SOM), radial bias function (RBF), genetic algorithms (GAS), neuro-fuzzy systems (NFS), adaptive resonance theory (ART), partial least squares (PLS), multiple linear regression (MLR), principal component regression (PCR), discriminant function analysis (DF A), linear discriminant analysis (LDA), cluster analysis, and nearest neighbor.

12. The system of claim 11, wherein the at least one algorithm is discriminant function analysis (DFA).

13. A method of diagnosing, monitoring, prognosing or staging Parkinson's disease in a subject, the method comprising the steps of:

(a) providing a system according to claim 1;
(b) exposing the at least one sensor to a test exhaled breath sample;
(c) measuring at least one response induced parameter from the at least one sensor upon exposure to the test sample to obtain a response pattern; and
(d) analyzing the response pattern obtained in step (c) using a learning and pattern recognition algorithm by comparing it to stored data obtained from a control sample whereby a significantly different response pattern of the test sample as compared to the control sample is indicative of Parkinson's disease, as well as its stage.

14. The method of claim 13, for differentiating between healthy subjects, subjects having early-stage Parkinson's disease, and subjects having advanced-stage Parkinson's disease.

15. The method of claim 13, further comprising the step of concentrating the test exhaled breath sample prior to step (b) using at least one of a breath concentrator and a dehumidifying unit.

16. The method of claim 13, wherein the response pattern is formed by the sensor detection of at least one volatile biomarker which is indicative of Parkinson's disease.

17. The system of claim 1, wherein the at least one sensor comprises Au nanoparticles capped with 3-mercapto-propionate.

18. A system for diagnosing, monitoring, prognosing or staging Parkinson's disease, the system comprising:

(a) an apparatus comprising at least one breath sensor comprising nanomaterials selected from the group consisting of SWCNTs coated with α-cyclodextrin, SWCNTs coated with carboxy-methylated β-cyclodextrin, SWCNTs coated with heptakis(2,3,6-tri-O-methyl)-β-cyclodextrin, Au nanoparticles capped with 3-mercapto-propionate, Au nanoparticles capped with 2-mercapto-benzoazole and Pt nanoparticles capped with 11-mercapto-1-undecanol; and
(b) a processing unit comprising a learning and pattern recognition analyzer wherein the learning and pattern recognition analyzer receives sensor output signals and compares them to stored data obtained from a control sample, whereby a significantly different sensor output signal as compared to the control sample is indicative of Parkinson's disease, wherein the control sample is a negative control sample, and wherein when the control sample is a sample of a subject with a known stage of Parkinson's disease, a significantly different sensor output compared to the control signal is indicative of a different stage of Parkinson's disease than the stage of Parkinson's disease in the control sample and wherein the processing unit is configured to present the resulting information on a display or to transmit said information to a host computer.

19. The system of claim 18, wherein the apparatus further comprises a sensor comprising SWCNTs coated with cyclodextrin, selected from the group consisting of β-cyclodextrin, γ-cyclodextrin, methyl-β-cyclodextrin, 2,6-dibutyl-β-cyclodextrin, hydroxypropyl-β-cyclodextrin, 2,6-di-O-methyl-β-cyclodextrin, permethylated α-cyclodextrin-6$^4$-monoalcohol nitrate, dinitrophenyl substituted β-cyclodextrin-based chiral stationary phases, β- and γ-cyclodextrins bearing 4-amino-7-nitrobenz-2-oxa-1,3-diazole functional groups, sulfated β-cyclodextrin, mono(6-cyclohexylamino-6-deoxy)-β-cyclodextrin, mono-(6-benzyl-imino-6-deoxy)-β-cyclodextrin, mono[6-(o-amino-phenyl)imino-6-deoxy]-β-cyclodextrin, mono[6-(p-aminophenyl)imino-6-deoxy]-β-cyclodextrin, mono[6-(α-naphthyl)imino-6-deoxy]-β- cyclodextrin, hexakis(6-O-benzoyl)-α-cyclodextrin, heptakis(2,3,6-tri-O-benzoyl)-β-cyclodextrin, hexakis(6-O-benzoyl-2,3-di-O-benzyl)-α-cyclodextrin, hexakis(2,3-di-O-benzyl)-α-cyclodextrin, 2-6-amino-β-cyclodextrin, permethylated-β-cyclodextrin, 2A,3A-Alloepithio-2A,3A-dideoxy-β-cyclodextrin, and combinations thereof.

20. The system of claim 18, wherein the apparatus further comprises a sensor comprising metal nanoparticles capped with an organic coating, wherein the metal nanoparticles are selected from the group consisting of Au, Ag, Ni, Co, Pt, Pd, Cu, and Al nanoparticles.

21. The system of claim 20, wherein the organic coating of the metal nanoparticles comprises compounds selected from the group consisting of alkylthiols, arylthiols, alkylarylthiols, alkylthiolates, ω-functionalized alkanethiolates, arenethiolates, (γ-mercaptopropyl)tri-methyloxysilane, dialkyl disulfides and combinations thereof.

22. The system of claim 18, wherein the Au and/or Pt nanoparticles have a morphology selected from a cubic, a spherical, and a spheroidal morphology.

23. The system of claim 18, wherein the at least one sensor is configured in a form selected from the group consisting of a capacitive sensor, a resistive sensor, an impedance sensor, and a field effect transistor sensor.

24. The system of claim 18, further comprising a detection device that measures changes in at least one property of the at least one sensor, wherein the detection device is selected from the group consisting of a resistance measurement device, a conductance measurement device, an alternating current (AC) measurement device, a frequency measurement device, a capacitance measurement device, an impedance measurement device, an inductance measurement device, a mobility measurement device, an electrical potential measurement device, an optical property measurement device, a voltage threshold measurement device, a fluorescence measurement device, a chemiluminescence measurement device, a phosphorescence measurement device, a bending measurement device, a surface acoustic wave measurement device, and a piezoelectricity measurement device.

25. The system of claim 18, wherein the learning and pattern recognition analyzer comprises at least one algorithm selected from the group consisting of artificial neural network algorithms, principal component analysis (PCA), multi-layer perception (MLP), generalized regression neural network (GRNN), fuzzy inference systems (FIS), self-organizing map (SOM), radial bias function (RBF), genetic algorithms (GAS), neuro-fuzzy systems (NFS), adaptive resonance theory (ART), partial least squares (PLS), multiple linear regression (MLR), principal component regression (PCR), discriminant function analysis (DF A), linear discriminant analysis (LDA), cluster analysis, and nearest neighbor.

* * * * *